US011877553B2

(12) United States Patent
Bernacchi et al.

(10) Patent No.: US 11,877,553 B2
(45) Date of Patent: Jan. 23, 2024

(54) EFFECTS OF A PLURALITY OF MUTATIONS TO IMPROVE HERBICIDE RESISTANCE/TOLERANCE IN RICE

(71) Applicant: RICETEC, INC., Alvin, TX (US)

(72) Inventors: Dario Bernacchi, Friendswood, TX (US); Caleb Knepper, League City, TX (US)

(73) Assignee: RiceTec, Inc., Alvin, TX (US)

( * ) Notice: Subject to any disclaimer, the term of this patent is extended or adjusted under 35 U.S.C. 154(b) by 359 days.

(21) Appl. No.: 15/863,559

(22) Filed: Jan. 5, 2018

(65) Prior Publication Data

US 2018/0216128 A1    Aug. 2, 2018

Related U.S. Application Data

(60) Provisional application No. 62/452,800, filed on Jan. 31, 2017, provisional application No. 62/453,094, filed on Feb. 1, 2017, provisional application No. 62/508,264, filed on May 18, 2017, provisional application No. 62/573,451, filed on Oct. 17, 2017.

(51) Int. Cl.
| | | |
|---|---|---|
| *A01H 6/46* | (2018.01) | |
| *A01H 5/10* | (2018.01) | |
| *A01N 43/50* | (2006.01) | |
| *C12N 15/82* | (2006.01) | |

(52) U.S. Cl.
CPC .......... *A01H 6/4636* (2018.05); *A01H 5/10* (2013.01); *A01N 43/50* (2013.01); *C12N 15/8274* (2013.01)

(58) Field of Classification Search
CPC .................................. C12N 15/8274
See application file for complete search history.

(56) References Cited

U.S. PATENT DOCUMENTS

| | | | |
|---|---|---|---|
| 5,378,824 A | 1/1995 | Bedbrook et al. | |
| 5,605,011 A | 2/1997 | Bedbrook et al. | |
| 5,736,629 A | 4/1998 | Croughan | |
| 5,773,704 A | 6/1998 | Croughan | |
| 5,952,553 A | 9/1999 | Croughan | |
| 6,211,438 B1 | 4/2001 | Anderson et al. | |
| 6,211,439 B1 | 4/2001 | Anderson et al. | |
| 6,222,100 B1 | 4/2001 | Anderson et al. | |
| 6,274,796 B1 | 8/2001 | Croughan | |
| 6,943,280 B2 * | 9/2005 | Croughan .......... | C12N 15/8278 536/23.6 |
| 7,119,256 B2 | 10/2006 | Shimizu et al. | |
| 7,399,905 B2 | 7/2008 | Croughan | |
| 8,017,400 B2 | 9/2011 | Toriyama et al. | |
| 8,030,547 B2 | 10/2011 | Kaku et al. | |
| 8,604,278 B2 | 12/2013 | Heim et al. | |
| 9,090,904 B2 | 7/2015 | Croughan | |
| 2003/0097692 A1 | 5/2003 | Jander et al. | |
| 2003/0217381 A1 | 11/2003 | Croughan | |
| 2003/0236208 A1 * | 12/2003 | Kmiec ................ | C12N 15/102 514/44 R |
| 2006/0010514 A1 | 1/2006 | Birk et al. | |
| 2006/0130172 A1 | 6/2006 | Whaley et al. | |
| 2010/0029485 A1 * | 2/2010 | Livore ................ | C12N 9/1022 800/300 |
| 2010/0287641 A1 | 11/2010 | McElver et al. | |
| 2011/0131679 A2 | 6/2011 | La Rosa et al. | |
| 2011/0252501 A1 | 10/2011 | Abad et al. | |
| 2012/0005773 A1 | 1/2012 | Aasen et al. | |
| 2012/0172224 A1 | 7/2012 | Livore et al. | |
| 2012/0233723 A1 | 9/2012 | Livore et al. | |
| 2013/0042366 A1 | 2/2013 | Mankin et al. | |
| 2013/0340114 A1 | 12/2013 | Albert et al. | |
| 2014/0135219 A1 | 5/2014 | Hain et al. | |
| 2014/0230086 A1 | 8/2014 | Linscombe | |
| 2014/0336051 A1 | 11/2014 | Schnabel et al. | |
| 2015/0029976 A1 | 1/2015 | Wang et al. | |
| 2015/0113676 A1 | 4/2015 | Abad et al. | |
| 2015/0197764 A1 | 7/2015 | Aasen et al. | |
| 2015/0216126 A1 | 8/2015 | Croughan | |
| 2015/0344902 A1 | 12/2015 | Croughan | |

FOREIGN PATENT DOCUMENTS

| | | |
|---|---|---|
| CN | 102559646 | 7/2012 |
| CN | 102559646 A | 7/2012 |
| EP | 1659855 | 11/2011 |
| WO | WO 2006/094084 | 9/2006 |

OTHER PUBLICATIONS

Walter et al, Pest Management Science (2014) 70:1831-1839.*
Duggleby et al, Plant Physiol. (2008) 48:309-324.*
Roso et al, Field Crop Res. (2010) 119:175-182.*
Okuzaki et al, Plant Cell Rep. (2004) 22:509-512.*
Endo et al., "Molecular breeding of a novel herbicide-tolerant rice by gene targeting," The Plant Journal, 52:157-166 (2007).
Goulart et al., "Identification of origin and analysis of population structure of field-selected imidazolinone-herbicide resistant red rice (*Oryza sativa*)," Eughytica (Jun. 17, 2012).
Kadaru, Suresh Babu, "Identification of molecular markers and association mapping of selected loci associated with agronomic traits in rice," Louisiana State University, LSU Digital Commons, retrieved from the Internet: https://digitalcommons.lsu.edu/cgo/viewcontent.cgi?article+1230&context=gradschool_dissertations (2007).
Powles et al., "Evolution in Action: Plants Resistant to Herbicides," Annu. Rev. Plant Biol., 61: 317-347 (2010).

(Continued)

*Primary Examiner* — Mykola V. Kovalenko

(74) *Attorney, Agent, or Firm* — Fox Rothschild LLP

(57) ABSTRACT

Rice is described that is tolerant/resistant to AHAS/ALS inhibitors because of a plurality of mutations that act synergistically in providing resistance/tolerance to the herbicide. Tolerance/resistance is due to presence of combined mutations in the rice leading to amino acid substitutions (A205V and G654E) in the AHAS/ALS enzyme. Use of the rice for weed control and methods of producing tolerant/resistant rice are also disclosed.

2 Claims, 17 Drawing Sheets
(16 of 17 Drawing Sheet(s) Filed in Color)
Specification includes a Sequence Listing.

(56) References Cited

OTHER PUBLICATIONS

Sudianto et al., "Clearfield® rice: Its development, success, and key challenges on a global perspective," Crop Protection, 49: 40-51 (2013).

Tan et al., "Herbicidal inhibitors of amino acid biosynthesis and herbicide-tolerant crops," Amino Acids, 30: 195-204 (2006).

Tan et al., "Imidazolinome-tolerant crops: history, current status and future," Pest Management Science, 61:246-257 (2005).

Search Report and Written Opinion issued in Int'l App. No. PCT/US2018/012609 (dated 2018).

Third-Party Preissuance Submission under 37 CFR 1.290 (Jan. 24, 2019).

McCourt et al., "Acetohydroxyacid synthase and its role in the biosynthetic pathway for branched-chain amino acids," Amino Acids, 31:173-210 (2006).

Wright et al., Cell selection and inheritance of imidazolinone resistance in sugarbeet (*Beta vulgaris*), Theor. Appl. Genet., 96:612-620 (1998).

Suresh Babu et al: "Identification of molecular markers and association mapping of selected loci associated with agronomic traits in rice". Publication: Jan. 1, 2007.

Tan S et al: "Imidazolinone-Tolerant Crops: History, Current Status and Future". Pest Management. 61(3): 246-257. Publication: Jan. 1, 2005.

Masaki Endo et al: "Molecular breeding of a novel herbicide-tolerant rice by gene targeting". The Plant Journal. 52(1): 157-166. Publication: Oct. 1, 2007.

Tan S et al: "Herbicidal inhibitors of amino acid biosynthesis and herbicide-tolerant crops". Amino Acids; The Forum for Amino Acid and Protein Research, Springerverlag. 30(2): 195-204. Publication: Mar. 1, 2006 (abstract).

Rosa et al., Regional scale distribution of imidazolinone herbicide-resistant alleles in red rice (*Oryza sativa* L.) determined through SNP markers, Field Crops Research, vol. 119, pp. 175-182, published on Dec. 31, 2010.

\* cited by examiner

FIG. 1 (cont.)

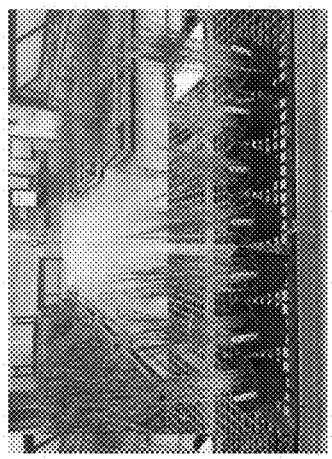
FIG. 3C
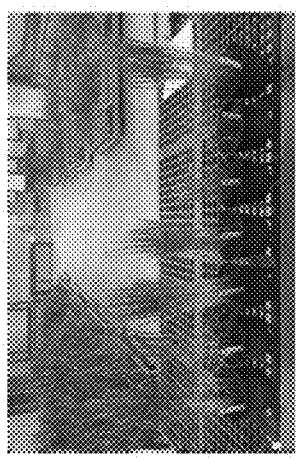
FIG. 3F
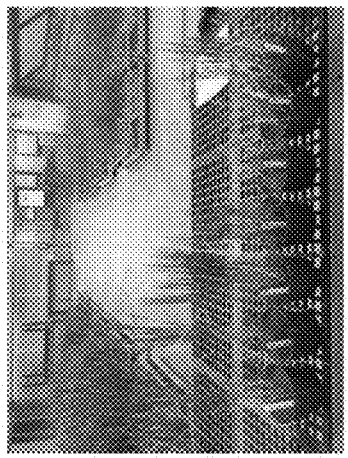
FIG. 3I
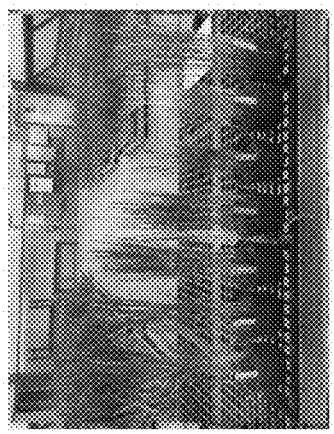
FIG. 3B
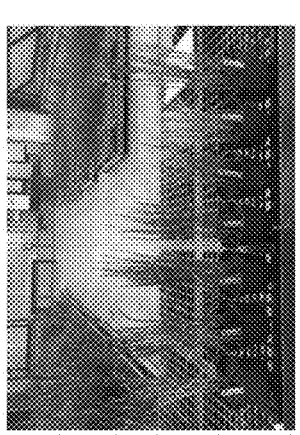
FIG. 3E
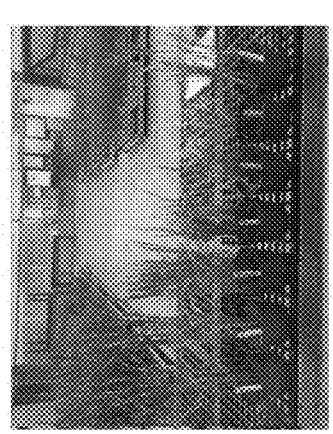
FIG. 3H
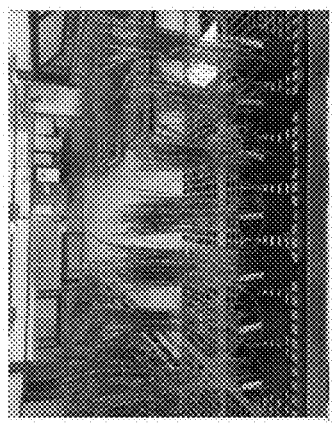
FIG. 3A
FIG. 3D
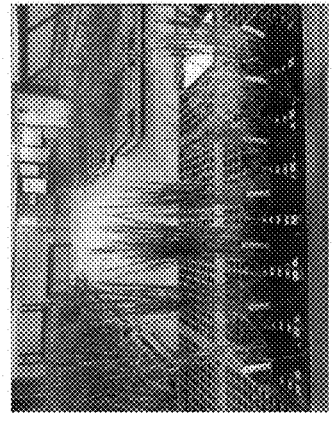
FIG. 3G

```
                      SEQUENCE LISTING

<160> NUMBER OF SEQ ID NOS: 13

<210> SEQ ID NO 1
<211> LENGTH: 2878
<212> TYPE: DNA
<213> ORGANISM: Oryza sativa

<400> SEQUENCE: 1
tgtaccctcc acccgttatt gggasggatc cacctgtcat cctcatccta tcaactgaca      60
cgcgggccca gatcgacccc gacgtggcag tgtgtcatcc tatcccaccg acatctgggg     120
cccaccgtga cgtggcccac acgatccat ccgagccaca catcgcctca cgctgcgtca     180
ccgcgcgcgg acaaaacacc cacaccccca cactctccac ccctctctct ctctctcgcc     240
caaacccaga aaccctcgcc gccgccgccg ccgccgccgc catcacccac catggctacg     300
accgccgcgg ccgcggccgc caccttgtcc gccgccgcga cggccaagac cggccgtaag     360
aaccaccagc gacaccacgt ccttcccgct cgaggccggg tggggcggc ggcggtcagg     420 tgctcggcgg tgtccccggt cacccccgcc tcccgcgc cgccggccac gccgctccgg     480 ccgtggggc cggccgagcc ccgcaagggc gcggacatcc tcgtggaggc gctggagcgg     540
tgcggcgtca gcgacgtgtt cgcctacccg ggcggcgcgt ccatggagat ccaccaggcg     600
ctgacgcgct ccccggtcat caccaaccac ctcttccgcc acgagcaggg cgaggcgttc     660
gcggcgtccg ggtacgcgcg cgcgtccggc cgcgtcgggg tctgcgtcgc cacctccggc     720
cccggggcaa ccaacctcgt gtccgcgctc gccgacgcgc tgctcgactc cgtcccgatg     780
gtcgccatca cgggccaggt cccccgccgc atgatcggca ccgacgcctt ccaggagacg     840
```

```
cccatagtcg aggtcacccg ctccatcacc aagcacaatt accttgtcct tgatgtggag      900
gacatccccc gcgtcataca ggaagccttc ttcctcgcgt cctcgggccg tcctggcccg      960
gtgctggtcg acatccccaa ggacatccag cagcagatgg ctgtgccagt ctgggacacc     1020
tcgatgaatc taccggggta cattgcacgc ctgcccaagc cacccgcgac agaattgctt     1080
gagcaggtct tgcgtctggt tggcgagtca cggcgcccga ttctctatgt cggtggtggc     1140
tgctctgcat ctggtgatga attgcgccgg tttgttgagc tgaccggcat cccagttaca     1200
accactctga tgggcctcgg caatttcccc agtgatgatc cgttgtccct gcgcatgctt     1260
gggatgcatg gcacggtgta cgcaaattat gcggtggata aggctgacct gttgcttgca     1320
tttggcgtgc ggtttgatga tcgtgtgaca gggaaaattg aggcttttgc aagcagggcc     1380
aagattgtgc acattgacat tgatccagcg gagattggaa agaacaagca accacatgtg     1440
tcaatttgcg cagatgttaa gcttgcttta cagggcttga atgctctgct agaccagagc     1500
acaacaaaga caagttctga ttttagtgca tggcacaatg agttggacca gcagaagagg     1560
gagtttcctc tggggtacaa gacttttggt gaagagatcc caccgcaata tgctattcag     1620
gtgctggatg agctgacgaa aggggaggca atcatcgcta ctggtgttgg acagcaccag     1680
atgtgggcgg cacaatatta cacctacaag cggccacggc agtggctgtc ttcggctggt     1740
ctgggcgcaa tgggatttgg gctgcctgct gcagctggtg cttctgtggc taacccaggt     1800
gtcacagttg ttgatattga tggggatggt agcttcctca tgaacattca ggagttggca     1860
ttgatccgca ttgagaacct cccggtgaag gtgatggtgt tgaacaacca acatttgggt     1920
atggttgtgc aatgggagga taggttttac aaggcaaata gggcgcatac atacttgggc     1980
aacccagaat gtgagagcga gatatatcca gattttgtga ctattgctaa agggttcaat     2040
attcctgcag tccgtgtaac aaagaagagt gaagtccgtg ccgccatcaa gaagatgctc     2100
gagaccccag ggcctatactt gttggatatc atcgtcccac accaggagca tgtgctgcct     2160
atgatcccaa gtggggcgc attcaaggac atgatcctgg atggtgatgg caggactatg     2220
tattaatcta taatctgtat gttggcaaag caccagcccg gcctatgttt gacctgaatg     2280
acccataaag agtggtatgc ctatgatgtt tgtatgtgct ctatcaataa ctaaggtgtc     2340
aactatgaac catatggtct tctgttttac ttgtttgatg tgcttggcat ggtaatccta     2400
attagcttcc tgctgtctag gtttgtagtg tgttgttttc cgtaggcata tgcatcacaa     2460
gatatcatgt aagtttcttg tcctacatat caataatgag aataaagtac ttctatgcaa     2520
tagctctgag ttaagtgttt caacaatttc tgaacttatg tttgctcagc actcagcagt     2580
catcacacga agtactctcc ttgtaactac attttcccaa agactttaaa tccccttagt     2640
tacagcaaaa aaataaaact ttgaatctat tgttttccct ctcttcggtc gatcttattg     2700
ggtacttcct ccgttattgg gtacttcctc cgtttcaggt tataagattt tctaacattg     2760
tccactttca tatagatgtt aaatgaattt agacatatgc tagaaagtct tataatctga     2820
aacgaaggta gtattattta tttgactact atagagagag gctgcatgaa gtatttcc       2878
```

<210> SEQ ID NO 2
<211> LENGTH: 2678
<212> TYPE: DNA
<213> ORGANISM: Oryza sativa

<400> SEQUENCE: 2

```
ctctytctyt ytcgcccaaa cccagaaacc ctcgccgccg ccgccgccgc cgccgccatc       60
```

```
acccaccatg gctacgaccg ccgcggccgc ggccgccacc ttgtccgccg ccgcgacggc    120
caagaccggc cgtaagaacc accagcgaca ccacgtcctt cccgctcgag gccgggtggg    180
ggcggcggcg gtcaggtgct cggcggtgtc cccggtcacc ccgccgtccc cggcgccgcc    240
ggccacgccg ctccggccgt gggggccggc cgagccccgc aagggcgcgg acatcctcgt    300
ggaggcgctg gagcggtgcg gcgtcagcga cgtgttcgcc tacccgggcg gcgcgtccat    360
ggagatccac caggcgctga cgcgctcccc ggtcatcacc aaccacctct ccgccacga    420 gcagggcgag gcgttcgcgg cgtccgggta cgcgcgcgcg tccggccgcg tcggggtctg    480
cgtcgccacc tccggccccg gggcaaccaa cctcgtgtcc gcgctcgccg acgcgctgct    540
cgactccgtc ccgatggtcg ccatcacggg ccaggtcccc cgccgcatga tcggcaccga    600
cgtcttccag gagacgccca tagtcgaggt cacccgctcc atcaccaagc acaattacct    660
tgtccttgat gtggaggaca tcccccgcgt catacaggaa gccttcttcc tcgcgtcctc    720
gggccgtcct ggcccggtgc tggtcgacat ccccaaggac atccagcagc agatggctgt    780
gccagtctgg gacacctcga tgaatctacc ggggtacatt gcacgcctgc caagccacc    840 cgcgacagaa ttgcttgagc aggtcttgcg tctggttggc gagtcacggc gcccgattct    900
ctatgtcggt ggtggctgct ctgcatctgg tgatgaattg cgccggtttg ttgagctgac    960
cggcatccca gttacaacca ctctgatggg cctcggcaat ttccccagtg atgatccgtt   1020
gtccctgcgc atgcttggga tgcatggcac ggtgtacgca aattatgcgg tggataaggc   1080
tgacctgttg cttgcatttg gcgtgcggtt tgatgatcgt gtgacaggga aaattgaggc   1140
ttttgcaagc agggccaaga ttgtgcacat tgacattgat ccagcggaga ttggaaagaa   1200
caagcaacca catgtgtcaa tttgcgcaga tgttaagctt gctttacagg cttgaatgc   1260 tctgctagac cagagcacaa caaagacaag ttctgatttt agtgcatggc acaatgagtt   1320
ggaccagcag aagagggagt ttcctctggg gtacaagact ttggtgaag agatcccacc   1380 gcaatatgct attcaggtgc tggatgagct gacgaaaggg gaggcaatca tcgctactgg   1440
tgttggacag caccagatgt gggcggcaca atattacacc tacaagcggc cacggcagtg   1500
gctgtcttcg gctggtctgg gcgcaatggg atttgggctg cctgctgcag ctggtgcttc   1560
tgtggctaac ccaggtgtca cagttgttga tattgatggg gatggtagct tcctcatgaa   1620
cattcaggag ttggcattga tccgcattga gaacctcccg gtgaaggtga tggtgttgaa   1680
caaccaacat ttgggtatgg ttgtgcaatg ggaggatagg ttttacaagg caaatagggc   1740
gcatacatac ttgggcaacc cagaatgtga gagcgagata tatccagatt ttgtgactat   1800
tgctaaaggg ttcaatattc ctgcagtccg tgtaacaaag aagagtgaag tccgtgccgc   1860
catcaagaag atgctcgaga ccccagggcc atacttgttg gatatcatcg tcccacacca   1920
ggagcatgtg ctgcctatga tcccaagtgg gggcgcattc aaggacatga tcctggatgg   1980
tgatggcagg actatgtatt aatctataat ctgtatgttg gcaaagcacc agcccggcct   2040
atgtttgacc tgaatgaccc ataaagagtg gtatgcctat gatgtttgta tgtgctctat   2100
caataactaa ggtgtcaact atgaaccata tggtcttctg ttttacttgt ttgatgtgct   2160
tggcatggta atcctaatta gcttcctgct gtctaggttt gtagtgtgtt gttttccgta   2220
ggcatatgca tcacaagata tcatgtaagt ttcttgtcct acatatcaat aatgagaata   2280
aagtacttct atgcaatagc tctgagttaa gtgtttcaac aatttctgaa cttatgtttg   2340
ctcagcactc agcagtcatc acacgaagta ctctccttgt aactacattt tcccaaagac   2400
tttaaatccc cttagttaca gcaaaaaaaa taaactttga atctattgtt ttccctctct   2460
```

```
tcggtcgatc ttattgggta cttcctccgt tattgggtac ttcctccgtt tcaggttata    2520
agattttcta acattgtcca cttttcatata gatgttaaat gaatttagac atatgctaga    2580
aagtcttata atctgaaacg aaggtagtat tatttatttg actactatag agagaggctg    2640
catgaagtat ttccttttc tgtttagttt ttgccgtg                              2678

<210> SEQ ID NO 3
<211> LENGTH: 2865
<212> TYPE: DNA
<213> ORGANISM: Oryza sativa

<400> SEQUENCE: 3
ctgtcatcct catcctatca actgacacgc gggcccagat cgaccccgac gtggcagtgt      60
gtcatcctat cccaccgaca tctgggggccc accgtgacgt ggcccacacg atcccatccg    120
agccacacat cgcctcacgc tgcgtcaccg cgcgcggaca aaacacccac accccacac     180 tctccaccc tctctctctc tctcgcccaa acccagaaac cctcgccgcc gccgccgccg      240
ccgccgccat cacccaccat ggctacgacc gccgcggccg cggccgccac cttgtccgcc    300
gccgcgacgg ccaagaccgg ccgtaagaac caccagcgac accacgtcct tcccgctcga     360
ggccgggtgg gggcggcggc ggtcaggtgc tcggcggtgt ccccggtcac cccgccgtcc    420
ccggcgccgc cggccacgcc gctccggccg tgggggccgg ccgagccccg caagggcgcg    480
gacatcctcg tggaggcgct ggagcggtgc ggcgtcagcg acgtgttcgc ctacccgggc    540
ggcgcgtcca tggagatcca ccaggcgctg acgcgctccc cggtcatcac caaccacctc   600
ttccgccacg agcagggcga ggcgttcgcg gcgtccgggt acgcgcgcgc gtccggccgc    660 gtcgggtct gcgtcgccac ctccggcccc ggggcaacca acctcgtgtc cgcgctcgcc    720
gacgcgctgc tcgactccgt cccgatggtc gccatcacgg gccaggtccc ccgccgcatg    780
atcggcaccg acgccttcca ggagacgccc atagtcgagg tcacccgctc catcaccaag    840
cacaattacc ttgtccttga tgtggaggac atccccgcg tcatacagga agccttcttc    900
ctcgcgtcct cgggccgtcc tggcccggtg ctggtcgaca tccccaagga catccagcag    960
cagatggctg tgccagtctg ggacacctcg atgaatctac cggggtacat tgcacgcctg   1020
cccaagccac ccgcgacaga attgcttgag caggtcttgc gtctggttgg cgagtcacgg    1080
cgcccgattc tctatgtcgg tggtggctgc tctgcatctg gtgatgaatt gcgcggtttt    1140
gttgagctga ccggcatccc agttacaacc actctgatgg gcctcggcaa tttccccagt   1200
gatgatccgt tgtccctgcg catgcttggg atgcatggca cggtgtacgc aaattatgcg    1260
gtggataagg ctgacctgtt gcttgcattt ggcgtgcggt ttgatgatcg tgtgacaggg    1320
aaaattgagg cttttgcaag cagggccaag attgtgcaca ttgacattga tccagcggag   1380
attggaaaga acaagcaacc acatgtgtca atttgcgcag atgttaagct tgctttacag    1440
ggcttgaatg ctctgctaga ccagagcaca acaaagacaa gttctgattt tagtgcatgg    1500
cacaatgagt tggaccagca gaagagggag tttcctctgg ggtacaagac ttttggtgaa    1560
gagatcccac cgcaatatgc tattcaggtg ctggatgagc tgacgaaagg ggaggcaatc   1620
atcgctactg gtgttggaca gcaccagatg tgggcggcac aatattacac ctacaagcgg    1680
ccacggcagt ggctgtcttc ggctggtctg ggcgcaatgg gatttgggct gcctgctgca    1740
gctggtgctt ctgtggctaa cccaggtgtc acagttgttg atattgatgg ggatggtagc    1800
ttcctcatga acattcagga gttggcattg atccgcattg agaacctccc ggtgaaggtg    1860
```

| | |
|---|---|
| atggtgttga caaccaaca tttgggtatg gttgtgcaat gggaggatag gttttacaag | 1920 |
| gcaaataggg cgcatacata cttgggcaac ccagaatgtg agagcgagat atatccagat | 1980 |
| tttgtgacta ttgctaaagg gttcaatatt cctgcagtcc gtgtaacaaa aagagtgaa | 2040 |
| gtccgtgccg ccatcaagaa gatgctcgag accccagggc catacttgtt ggatatcatc | 2100 |
| gtcccacacc aggagcatgt gctgcctatg atcccaagtg ggggcgcatt caaggacatg | 2160 |
| atcctggatg gtgatggcag gactatgtat taatctataa tctgtatgtt ggcaaagcac | 2220 |
| cagcccggcc tatgtttgac ctgaatgacc cataaagagt ggtatgccta tgatgtttgt | 2280 |
| atgtgctcta tcaataacta aggtgtcaac tatgaaccat atggtcttct gttttacttg | 2340 |
| tttgatgtgc ttggcatggt aatcctaatt agcttcctgc tgtctaggtt tgtagtgtgt | 2400 |
| tgttttccgt aggcatatgc atcacaagat atcatgtaag tttcttgtcc tacatatcaa | 2460 |
| taatgagaat aaagtacttc tatgcaatag ctctgagtta agtgtttcaa caatttctga | 2520 |
| acttatgttt gctcagcact cagcagtcat cacacgaagt actctccttg taactacatt | 2580 |
| ttcccaaaga ctttaaatcc ccttagttac agcaaaaaaa ataaactttg aatctattgt | 2640 |
| tttccctctc ttcggtcgat cttattgggt acttcctccg ttattgggta cttcctccgt | 2700 |
| ttcaggttat aagattttct aacattgtcc actttcatat agatgttaaa tgaatttaga | 2760 |
| catatgctag aaagtcttat aatctgaaac gaaggtagta ttatttattt gactactata | 2820 |
| gagagaggct gcatgaagta tttcctttt ctgtttagtt ttgcc | 2865 |

<210> SEQ ID NO 4
<211> LENGTH: 2877
<212> TYPE: DNA
<213> ORGANISM: Oryza sativa

<400> SEQUENCE: 4

| | |
|---|---|
| agttytgtac cctccacccg ttattgggas ggatccacct gtcatcctca tcctatcaac | 60 |
| tgacacgcgg gcccagatcg accccgacgt ggcagtgtgt catcctatcc caccgacatc | 120 |
| tggggcccac cgtgacgtgg cccacacgat cccatccgag ccacacatcg cctcacgctg | 180 |
| cgtcaccgcg cgcggacaaa acacccacac ccccacactc tccaccccctc tctctctctc | 240 |
| tcgcccaaac ccagaaaccc tcgccgccgc cgccgccgcc gccgccatca cccaccatgg | 300 |
| ctacgaccgc cgcggccgcg gccgccacct tgtccgccgc cgcgacggcc aagaccggcc | 360 |
| gtaagaacca ccagcgacac cacgtccttc ccgctcgagg ccgggtgggg cggcggcgg | 420 |
| tcaggtgctc ggcggtgtcc ccggtcaccc cgccgtcccc ggcgccgccg ccacgccgc | 480 |
| tccggccgtg ggggccggcc gagccccgca agggcgcgga catcctcgtg gaggcgctgg | 540 |
| agcggtgcgg cgtcagcgac gtgttcgcct accgggcgg cgcgtccatg gagatccacc | 600 |
| aggcgctgac gcgctccccg gtcatcacca accacctctt ccgccacgag cagggcgagg | 660 |
| cgttcgcggc gtccgggtac gcgcgcgcgt ccggccgcgt cggggtctgc gtcgccacct | 720 |
| ccggccccgg ggcaaccaac ctcgtgtccg cgctcgccga cgcgctgctc gactccgtcc | 780 |
| cgatggtcgc catcacgggc caggtccccc gccgcatgat cggcaccgac gccttccagg | 840 |
| agacgcccat agtcgaggtc acccgctcca tcaccaagca caattccctt gtccttgatg | 900 |
| tggaggacat ccccgcgtc atacaggaag ccttcttcct cgcgtcctcg gccgtcctg | 960 |
| gcccggtgct ggtcgacatc cccaaggaca tccagcagca gatggctgtg ccagtctggg | 1020 |
| acacctcgat gaatctaccg gggtacattg cacgcctgcc caagccaccc gcgacagaat | 1080 |
| tgcttgagca ggtcttgcgt ctggttggcg agtcacggcg cccgattctc tatgtcggtg | 1140 |

-continued

```
gtggctgctc tgcatctggt gatgaattgc gccggtttgt tgagctgacc ggcatcccag    1200
ttacaaccac tctgatgggc ctcggcaatt tccccagtga tgatccgttg tccctgcgca    1260
tgcttgggat gcatggcacg gtgtacgcaa attatgcggt ggataaggct gacctgttgc    1320
ttgcatttgg cgtgcggttt gatgatcgtg tgacagggaa aattgaggct tttgcaagca    1380
gggccaagat tgtgcacatt gacattgatc cagcggagat tggaaagaac aagcaaccac    1440
atgtgtcaat ttgcgcagat gttaagcttg ctttacaggg cttgaatgct ctgctagacc    1500
agagcacaac aaagacaagt tctgatttta gtgcatggca caatgagttg gaccagcaga    1560
agagggagtt tcctctgggg tacaagactt ttggtgaaga gatcccaccg caatatgcta    1620
ttcaggtgct ggatgagctg acgaaagggg aggcaatcat cgctactggt gttggacagc    1680
accagatgtg ggcggcacaa tattacacct acaagcggcc acggcagtgg ctgtcttcgg    1740
ctggtctggg cgcaatggga tttgggctgc ctgctgcagc tggtgcttct gtggctaacc    1800
caggtgtcac agttgttgat attgatgggg atggtagctt cctcatgaac attcaggagt    1860
tggcattgat ccgcattgag aacctcccgg tgaaggtgat ggtgttgaac aaccaacatt    1920
tgggtatggt tgtgcaatgg gaggataggt tttacaaggc aaatagggcg catacatact    1980
tgggcaaccc agaatgtgag agcgagatat atccagattt tgtgactatt gctaaagggt    2040
tcaatattcc tgcagtccgt gtaacaaaga gagtgaagtc ccgtgccgcc atcaagaaga    2100
tgctcgagac cccagggcca tacttgttgg atatcatcgt cccacaccag gagcatgtgc    2160
tgcctatgat cccaagtgag ggcgcattca aggacatgat cctggatggt gatggcagga    2220
ctatgtatta atctataatc tgtatgttgg caaagcacca gcccggccta tgtttgacct    2280
gaatgaccca taaagagtgg tatgcctatg atgtttgtat gtgctctatc aataactaag    2340
gtgtcaacta tgaaccgtat ggtcttctgt tttacttgtt tgatgtgctt ggcatggtaa    2400
tcctaattag cttcctgctg tctaggtttg tagtgtgttg ttttccgtag gcatatgcat    2460
cacaagatat catgtaagtt tcttgtccta catatcaata atgagaataa agtacttcta    2520
tgcaatagct ctgagttaag tgtttcaaca atttctgaac ttatgtttgc tcagcactca    2580
gcagtcatca cacgaagtac tctccttgta actacatttt cccaaagact ttaaatcccc    2640
ttagttacag caaaaaaaat aaactttgaa tctattgttt tccctctctt cggtcgatct    2700
tattgggtac ttcctccgtt attgggtact tcctccgttt caggttataa gattttctaa    2760
cattgtccac tttcatatag atgttaaatg aatttagaca tatgctagaa agtcttataa    2820
tctgaaacga aggtagtatt atttatttga ctactataga gagaggctgc atgaagt      2877
```

<210> SEQ ID NO 5
<211> LENGTH: 644
<212> TYPE: PRT
<213> ORGANISM: Oryza sativa

<400> SEQUENCE: 5

```
Met Ala Thr Thr Ala Ala Ala Ala Ala Thr Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60
```

```
Trp Gly Pro Ala Glu Pro Arg Lys Gly Ala Asp Ile Leu Val Glu Ala
 65                  70                  75                  80

Leu Glu Arg Cys Gly Val Ser Asp Val Phe Ala Tyr Pro Gly Gly Ala
             85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
        130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Val Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Arg Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
                405                 410                 415

Glu Leu Asp Gln Gln Lys Arg Gln Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
```

```
                    485             490                 495
Ala Ser Val Ala Asn Pro Gly Val Thr Val Asp Ile Asp Gly Asp
            500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
            530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
                580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
            610                 615                 620

Ile Pro Ser Gly Gly Ala Phe Lys Asp Met Ile Leu Asp Gly Asp Gly
625                 630                 635                 640

Arg Thr Met Tyr

<210> SEQ ID NO 6
<211> LENGTH: 644
<212> TYPE: PRT
<213> ORGANISM: Oryza sativa

<400> SEQUENCE: 6

Met Ala Thr Thr Ala Ala Ala Ala Ala Thr Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
            35                  40                  45

Pro Val Thr Pro Pro Ser Pro Ala Pro Pro Ala Thr Pro Leu Arg Pro
50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
            130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
            195                 200                 205

Ile Gln Glu Ala Phe Phe Leu Ala Ser Ser Gly Arg Pro Gly Pro Val
```

-continued

```
            210                 215                 220
Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                    245                 250                 255

Pro Pro Ala Thr Glu Leu Leu Glu Gln Val Leu Arg Leu Val Gly Glu
                260                 265                 270

Ser Arg Arg Pro Ile Leu Tyr Val Gly Gly Cys Ser Ala Ser Gly
            275                 280                 285

Asp Glu Leu Arg Arg Phe Val Glu Leu Thr Gly Ile Pro Val Thr Thr
        290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                    325                 330                 335

Lys Ala Asp Leu Leu Leu Ala Phe Gly Val Arg Phe Asp Asp Arg Val
                340                 345                 350

Thr Gly Lys Ile Glu Ala Phe Ala Ser Arg Ala Lys Ile Val His Ile
            355                 360                 365

Asp Ile Asp Pro Ala Glu Ile Gly Lys Asn Lys Gln Pro His Val Ser
        370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
                    405                 410                 415

Glu Leu Asp Gln Gln Lys Arg Glu Phe Pro Leu Gly Tyr Lys Thr Phe
                420                 425                 430

Gly Glu Glu Ile Pro Pro Gln Tyr Ala Ile Gln Val Leu Asp Glu Leu
            435                 440                 445

Thr Lys Gly Glu Ala Ile Ile Ala Thr Gly Val Gly Gln His Gln Met
        450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Gly
                    485                 490                 495

Ala Ser Val Ala Asn Pro Gly Val Thr Val Asp Ile Asp Gly Asp
                500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
        530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                    565                 570                 575

Thr Ile Ala Lys Gly Phe Asn Ile Pro Ala Val Arg Val Thr Lys Lys
                580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
        610                 615                 620

Ile Pro Asn Gly Gly Ala Phe Lys Asp Met Ile Leu Asp Gly Asp Gly
625                 630                 635                 640
```

Arg Thr Met Tyr

<210> SEQ ID NO 7
<211> LENGTH: 644
<212> TYPE: PRT
<213> ORGANISM: Oryza sativa

<400> SEQUENCE: 7

| | | | | | | | | | | | | | | | |
|---|---|---|---|---|---|---|---|---|---|---|---|---|---|---|---|
| Met | Ala | Thr | Thr | Ala | Ala | Ala | Ala | Ala | Thr | Leu | Ser | Ala | Ala | Ala | |
| 1 | | | | 5 | | | | | 10 | | | | | 15 | |
| Thr | Ala | Lys | Thr | Gly | Arg | Lys | Asn | His | Gln | Arg | His | His | Val | Leu | Pro |
| | | | 20 | | | | | 25 | | | | | 30 | | |
| Ala | Arg | Gly | Arg | Val | Gly | Ala | Ala | Val | Arg | Cys | Ser | Ala | Val | Ser | |
| | | | 35 | | | | 40 | | | | | 45 | | | |
| Pro | Val | Thr | Pro | Pro | Ser | Pro | Ala | Pro | Pro | Ala | Thr | Pro | Leu | Arg | Pro |
| | | 50 | | | | | 55 | | | | | 60 | | | |
| Trp | Gly | Pro | Ala | Glu | Pro | Arg | Lys | Gly | Ala | Asp | Ile | Leu | Val | Glu | Ala |
| 65 | | | | | 70 | | | | | 75 | | | | | 80 |
| Leu | Glu | Arg | Cys | Gly | Val | Ser | Asp | Val | Phe | Ala | Tyr | Pro | Gly | Gly | Ala |
| | | | | 85 | | | | | 90 | | | | | 95 | |
| Ser | Met | Glu | Ile | His | Gln | Ala | Leu | Thr | Arg | Ser | Pro | Val | Ile | Thr | Asn |
| | | | | 100 | | | | | 105 | | | | | 110 | |
| His | Leu | Phe | Arg | His | Glu | Gln | Gly | Glu | Ala | Phe | Ala | Ala | Ser | Gly | Tyr |
| | | | 115 | | | | | 120 | | | | | 125 | | |
| Ala | Arg | Ala | Ser | Gly | Arg | Val | Gly | Val | Cys | Val | Ala | Thr | Ser | Gly | Pro |
| | | 130 | | | | | 135 | | | | | 140 | | | |
| Gly | Ala | Thr | Asn | Leu | Val | Ser | Ala | Leu | Ala | Asp | Ala | Leu | Leu | Asp | Ser |
| 145 | | | | | 150 | | | | | 155 | | | | | 160 |
| Val | Pro | Met | Val | Ala | Ile | Thr | Gly | Gln | Val | Pro | Arg | Arg | Met | Ile | Gly |
| | | | | 165 | | | | | 170 | | | | | 175 | |
| Thr | Asp | Ala | Phe | Gln | Glu | Thr | Pro | Ile | Val | Glu | Val | Thr | Arg | Ser | Ile |
| | | | 180 | | | | | 185 | | | | | 190 | | |
| Thr | Lys | His | Asn | Tyr | Leu | Val | Leu | Asp | Val | Glu | Asp | Ile | Pro | Arg | Val |
| | | 195 | | | | | 200 | | | | | 205 | | | |
| Ile | Gln | Glu | Ala | Phe | Phe | Leu | Ala | Ser | Ser | Gly | Arg | Pro | Gly | Pro | Val |
| | 210 | | | | | 215 | | | | | 220 | | | | |
| Leu | Val | Asp | Ile | Pro | Lys | Asp | Ile | Gln | Gln | Gln | Met | Ala | Val | Pro | Val |
| 225 | | | | | 230 | | | | | 235 | | | | | 240 |
| Trp | Asp | Thr | Ser | Met | Asn | Leu | Pro | Gly | Tyr | Ile | Ala | Arg | Leu | Pro | Lys |
| | | | | 245 | | | | | 250 | | | | | 255 | |
| Pro | Pro | Ala | Thr | Glu | Leu | Leu | Glu | Gln | Val | Leu | Arg | Leu | Val | Gly | Glu |
| | | | 260 | | | | | 265 | | | | | 270 | | |
| Ser | Arg | Arg | Pro | Ile | Leu | Tyr | Val | Gly | Gly | Gly | Cys | Ser | Ala | Ser | Gly |
| | | 275 | | | | | 280 | | | | | 285 | | | |
| Asp | Glu | Leu | Arg | Arg | Phe | Val | Glu | Leu | Thr | Gly | Ile | Pro | Val | Thr | Thr |
| | 290 | | | | | 295 | | | | | 300 | | | | |
| Thr | Leu | Met | Gly | Leu | Gly | Asn | Phe | Pro | Ser | Asp | Asp | Pro | Leu | Ser | Leu |
| 305 | | | | | 310 | | | | | 315 | | | | | 320 |
| Arg | Met | Leu | Gly | Met | His | Gly | Thr | Val | Tyr | Ala | Asn | Tyr | Ala | Val | Asp |
| | | | | 325 | | | | | 330 | | | | | 335 | |
| Lys | Ala | Asp | Leu | Leu | Leu | Ala | Phe | Gly | Val | Arg | Phe | Asp | Asp | Arg | Val |
| | | | 340 | | | | | 345 | | | | | 350 | | |
| Thr | Gly | Lys | Ile | Glu | Ala | Phe | Ala | Ser | Arg | Ala | Lys | Ile | Val | His | Ile |
| | | 355 | | | | | 360 | | | | | 365 | | | |

-continued

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
    530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ser Glu Gly Ala Phe Lys Asp Met Ile Leu Asp Gly Asp Gly
625                 630                 635                 640

Arg Thr Met Tyr

<210> SEQ ID NO 8
<211> LENGTH: 644
<212> TYPE: PRT
<213> ORGANISM: Oryza sativa

<400> SEQUENCE: 8

Met Ala Thr Thr Ala Ala Ala Ala Ala Thr Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

```
Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
            115                 120                 125

Ala Arg Ala Ser Gly Arg Val Gly Val Cys Val Ala Thr Ser Gly Pro
        130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Arg Phe Val Glu Leu Thr Gly Ile Pro Val Thr Thr
290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510
```

```
Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
        530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Asn Gly Gly Ala Phe Lys Asp Met Ile Leu Asp Gly Asp Gly
625                 630                 635                 640

Arg Thr Met Tyr

<210> SEQ ID NO 9
<211> LENGTH: 644
<212> TYPE: PRT
<213> ORGANISM: Oryza sativa

<400> SEQUENCE: 9

Met Ala Thr Thr Ala Ala Ala Ala Ala Thr Leu Ser Ala Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240
```

Trp Asp Thr Ser Met Asn Leu Pro Gly Tyr Ile Ala Arg Leu Pro Lys
            245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Cys Ser Ala Ser Gly
            275                 280                 285

Asp Glu Leu Arg Arg Phe Val Glu Leu Thr Gly Ile Pro Val Thr Thr
            290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                    325                 330                 335

Lys Ala Asp Leu Leu Leu Ala Phe Gly Val Arg Phe Asp Asp Arg Val
                    340                 345                 350

Thr Gly Lys Ile Glu Ala Phe Ala Ser Arg Ala Lys Ile Val His Ile
                    355                 360                 365

Asp Ile Asp Pro Ala Glu Ile Gly Lys Asn Lys Gln Pro His Val Ser
                    370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
                    405                 410                 415

Glu Leu Asp Gln Gln Lys Arg Glu Phe Pro Leu Gly Tyr Lys Thr Phe
                    420                 425                 430

Gly Glu Glu Ile Pro Pro Gln Tyr Ala Ile Gln Val Leu Asp Glu Leu
                    435                 440                 445

Thr Lys Gly Glu Ala Ile Ile Ala Thr Gly Val Gly Gln His Gln Met
            450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                    485                 490                 495

Ala Ser Val Ala Asn Pro Gly Val Thr Val Val Asp Ile Asp Gly Asp
                    500                 505                 510

Gly Ser Phe Leu Met Asn Ile Gln Glu Leu Ala Leu Ile Arg Ile Glu
            515                 520                 525

Asn Leu Pro Val Lys Val Met Val Leu Asn Asn Gln His Leu Gly Met
            530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                    565                 570                 575

Thr Ile Ala Lys Gly Phe Asn Ile Pro Ala Val Arg Val Thr Lys Lys
                    580                 585                 590

Ser Glu Val Arg Ala Ala Ile Lys Lys Met Leu Glu Thr Pro Gly Pro
            595                 600                 605

Tyr Leu Leu Asp Ile Ile Val Pro His Gln Glu His Val Leu Pro Met
            610                 615                 620

Ile Pro Ser Gly Gly Ala Phe Lys Asp Met Ile Leu Asp Gly Asp Gly
625                 630                 635                 640

Arg Thr Met Tyr

<210> SEQ ID NO 10

```
<211> LENGTH: 644
<212> TYPE: PRT
<213> ORGANISM: Oryza sativa

<400> SEQUENCE: 10

Met Ala Thr Thr Ala Ala Ala Ala Ala Thr Leu Ser Ala Ala Ala
1               5                   10                  15

Thr Ala Lys Thr Gly Arg Lys Asn His Gln Arg His Val Leu Pro
            20                  25                  30

Ala Arg Gly Arg Val Gly Ala Ala Val Arg Cys Ser Ala Val Ser
        35                  40                  45

Pro Val Thr Pro Pro Ser Pro Ala Pro Pro Ala Thr Pro Leu Arg Pro
    50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Gly Cys Ser Ala Ser Gly
        275                 280                 285

Asp Glu Leu Arg Arg Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
```

-continued

```
            385                 390                 395                 400
        Asp Gln Ser Thr Thr Lys Thr Ser Asp Phe Ser Ala Trp His Asn
                        405                 410                 415

Glu Leu Asp Gln Gln Lys Arg Glu Phe Pro Leu Gly Tyr Lys Thr Phe
                        420                 425                 430

Gly Glu Glu Ile Pro Pro Gln Tyr Ala Ile Gln Val Leu Asp Glu Leu
                        435                 440                 445

Thr Lys Gly Glu Ala Ile Ile Ala Thr Gly Val Gly Gln His Gln Met
                    450                 455                 460

Trp Ala Ala Gln Tyr Tyr Thr Tyr Lys Arg Pro Arg Gln Trp Leu Ser
        465                 470                 475                 480

Ser Ala Gly Leu Gly Ala Met Gly Phe Gly Leu Pro Ala Ala Ala Gly
                            485                 490                 495

Ala Ser Val Ala Asn Pro Gly Val Thr Val Asp Ile Asp Gly Asp
                        500                 505                 510

Gly Ser Phe Leu Met Asn Ile Gln Glu Leu Ala Leu Ile Arg Ile Glu
                    515                 520                 525

Asn Leu Pro Val Lys Val Met Val Leu Asn Asn Gln His Leu Gly Met
                530                 535                 540

Val Val Gln Trp Glu Asp Arg Phe Tyr Lys Ala Asn Arg Ala His Thr
        545                 550                 555                 560

Tyr Leu Gly Asn Pro Glu Cys Glu Ser Glu Ile Tyr Pro Asp Phe Val
                        565                 570                 575

Thr Ile Ala Lys Gly Phe Asn Ile Pro Ala Val Arg Val Thr Lys Lys
                    580                 585                 590

Ser Glu Val Arg Ala Ala Ile Lys Lys Met Leu Glu Thr Pro Gly Pro
                595                 600                 605

Tyr Leu Leu Asp Ile Ile Val Pro His Gln Glu His Val Leu Pro Met
                610                 615                 620

Ile Pro Ser Gly Gly Ala Phe Lys Asp Met Ile Leu Asp Gly Asp Gly
        625                 630                 635                 640

Arg Thr Met Tyr

<210> SEQ ID NO 11
<211> LENGTH: 644
<212> TYPE: PRT
<213> ORGANISM: Oryza sativa

<400> SEQUENCE: 11

Met Ala Thr Thr Ala Ala Ala Ala Ala Thr Leu Ser Ala Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
            35                  40                  45

Pro Val Thr Pro Pro Ser Pro Ala Pro Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
```

-continued

```
            115                 120                 125
Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270

Ser Arg Arg Pro Ile Leu Tyr Val Gly Gly Cys Ser Ala Ser Gly
        275                 280                 285

Asp Glu Leu Arg Arg Phe Val Glu Leu Thr Gly Ile Pro Val Thr Thr
    290                 295                 300

Thr Leu Met Gly Leu Gly Asn Phe Pro Ser Asp Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
    370                 375                 380

Ile Cys Ala Asp Val Lys Leu Ala Leu Gln Gly Leu Asn Ala Leu Leu
385                 390                 395                 400

Asp Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
    450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
    530                 535                 540
```

```
Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
    610                 615                 620

Ile Pro Ser Gly Gly Ala Phe Lys Asp Met Ile Leu Asp Gly Asp Gly
625                 630                 635                 640

Arg Thr Met Tyr

<210> SEQ ID NO 12
<211> LENGTH: 644
<212> TYPE: PRT
<213> ORGANISM: Oryza sativa

<400> SEQUENCE: 12

Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
                20                  25                  30

Ala Arg Gly Arg Val Gly Ala Ala Val Arg Cys Ser Ala Val Ser
            35                  40                  45

Pro Val Thr Pro Pro Ser Pro Ala Pro Pro Ala Thr Pro Leu Arg Pro
        50                  55                  60

Trp Gly Pro Ala Glu Pro Arg Lys Gly Ala Asp Ile Leu Val Glu Ala
65                  70                  75                  80

Leu Glu Arg Cys Gly Val Ser Asp Val Phe Ala Tyr Pro Gly Gly Ala
                85                  90                  95

Ser Met Glu Ile His Gln Ala Leu Thr Arg Ser Pro Val Ile Thr Asn
            100                 105                 110

His Leu Phe Arg His Glu Gln Gly Glu Ala Phe Ala Ala Ser Gly Tyr
        115                 120                 125

Ala Arg Ala Ser Gly Arg Val Gly Val Cys Val Ala Thr Ser Gly Pro
    130                 135                 140

Gly Ala Thr Asn Leu Val Ser Ala Leu Ala Asp Ala Leu Leu Asp Ser
145                 150                 155                 160

Val Pro Met Val Ala Ile Thr Gly Gln Val Pro Arg Arg Met Ile Gly
                165                 170                 175

Thr Asp Ala Phe Gln Glu Thr Pro Ile Val Glu Val Thr Arg Ser Ile
            180                 185                 190

Thr Lys His Asn Tyr Leu Val Leu Asp Val Glu Asp Ile Pro Arg Val
        195                 200                 205

Ile Gln Glu Ala Phe Phe Leu Ala Ser Ser Gly Arg Pro Gly Pro Val
    210                 215                 220

Leu Val Asp Ile Pro Lys Asp Ile Gln Gln Met Ala Val Pro Val
225                 230                 235                 240

Trp Asp Thr Ser Met Asn Leu Pro Gly Tyr Ile Ala Arg Leu Pro Lys
                245                 250                 255

Pro Pro Ala Thr Glu Leu Leu Glu Gln Val Leu Arg Leu Val Gly Glu
            260                 265                 270
```

Ser Arg Arg Pro Ile Leu Tyr Val Gly Gly Cys Ser Ala Ser Gly
        275                 280                 285

Asp Glu Leu Arg Trp Phe Val Glu Leu Thr Gly Ile Pro Val Thr Thr
290                 295                 300

Thr Leu Met Gly Leu Gly Asn Phe Pro Ser Asp Pro Leu Ser Leu
305                 310                 315                 320

Arg Met Leu Gly Met His Gly Thr Val Tyr Ala Asn Tyr Ala Val Asp
                325                 330                 335

Lys Ala Asp Leu Leu Leu Ala Phe Gly Val Arg Phe Asp Asp Arg Val
            340                 345                 350

Thr Gly Lys Ile Glu Ala Phe Ala Ser Arg Ala Lys Ile Val His Ile
        355                 360                 365

Asp Ile Asp Pro Ala Glu Ile Gly Lys Asn Lys Gln Pro His Val Ser
370                 375                 380

Ile Cys Ala Asp Val Lys Leu Ala Leu Gln Gly Leu Asn Ala Leu Leu
385                 390                 395                 400

Gln Gln Ser Thr Thr Lys Thr Ser Ser Asp Phe Ser Ala Trp His Asn
                405                 410                 415

Glu Leu Asp Gln Gln Lys Arg Glu Phe Pro Leu Gly Tyr Lys Thr Phe
            420                 425                 430

Gly Glu Glu Ile Pro Pro Gln Tyr Ala Ile Gln Val Leu Asp Glu Leu
        435                 440                 445

Thr Lys Gly Glu Ala Ile Ile Ala Thr Gly Val Gly Gln His Gln Met
450                 455                 460

Trp Ala Ala Gln Tyr Tyr Thr Tyr Lys Arg Pro Arg Gln Trp Leu Ser
465                 470                 475                 480

Ser Ala Gly Leu Gly Ala Met Gly Phe Gly Leu Pro Ala Ala Ala Gly
                485                 490                 495

Ala Ser Val Ala Asn Pro Gly Val Thr Val Val Asp Ile Asp Gly Asp
            500                 505                 510

Gly Ser Phe Leu Met Asn Ile Gln Glu Leu Ala Leu Ile Arg Ile Glu
        515                 520                 525

Asn Leu Pro Val Lys Val Met Val Leu Asn Asn Gln His Leu Gly Met
530                 535                 540

Val Val Gln Trp Glu Asp Arg Phe Tyr Lys Ala Asn Arg Ala His Thr
545                 550                 555                 560

Tyr Leu Gly Asn Pro Glu Cys Glu Ser Glu Ile Tyr Pro Asp Phe Val
                565                 570                 575

Thr Ile Ala Lys Gly Phe Asn Ile Pro Ala Val Arg Val Thr Lys Lys
            580                 585                 590

Ser Glu Val Arg Ala Ala Ile Lys Lys Met Leu Glu Thr Pro Gly Pro
        595                 600                 605

Tyr Leu Leu Asp Ile Ile Val Pro His Gln Glu His Val Leu Pro Met
610                 615                 620

Ile Pro Ser Gly Gly Ala Phe Lys Asp Met Ile Leu Asp Gly Asp Gly
625                 630                 635                 640

Arg Thr Val Tyr

<210> SEQ ID NO 13
<211> LENGTH: 669
<212> TYPE: PRT
<213> ORGANISM: Arabidopsis thaliana

<400> SEQUENCE: 13

```
Met Ala Ala Thr Thr Thr Thr Thr Ser Ser Ile Ser Phe
1               5                   10              15

Ser Thr Lys Pro Ser Pro Ser Ser Lys Ser Pro Leu Pro Ile Ser
            20              25              30

Arg Phe Ser Leu Pro Phe Ser Leu Asn Pro Asn Lys Ser Ser Ser
        35              40              45

Ser Arg Arg Arg Gly Ile Lys Ser Ser Ser Pro Ser Ser Ile Ser Ala
    50              55              60

Val Leu Asn Thr Thr Thr Asn Val Thr Thr Thr Pro Ser Pro Thr Lys
65              70              75              80

Pro Thr Lys Pro Glu Thr Phe Ile Ser Arg Phe Ala Pro Asp Gln Pro
                85                  90              95

Arg Lys Gly Ala Asp Ile Leu Val Glu Ala Leu Glu Arg Gln Gly Val
            100             105             110

Glu Thr Val Phe Ala Tyr Pro Gly Gly Ala Ser Met Glu Ile His Gln
        115             120             125

Ala Leu Thr Arg Ser Ser Ser Ile Arg Asn Val Leu Pro Arg His Glu
    130             135             140

Gln Gly Gly Val Phe Ala Ala Glu Gly Tyr Ala Arg Ser Ser Gly Lys
145             150             155             160

Pro Gly Ile Cys Ile Ala Thr Ser Gly Pro Gly Ala Thr Asn Leu Val
                165             170             175

Ser Gly Leu Ala Asp Ala Leu Leu Asp Ser Val Pro Leu Val Ala Ile
            180             185             190

Thr Gly Gln Val Pro Arg Arg Met Ile Gly Thr Asp Ala Phe Gln Glu
        195             200             205

Thr Pro Ile Val Glu Val Thr Arg Ser Ile Thr Lys His Asn Tyr Leu
    210             215             220

Val Met Asp Val Glu Asp Ile Pro Arg Ile Ile Glu Glu Ala Phe Phe
225             230             235             240

Leu Ala Thr Ser Gly Arg Pro Gly Pro Val Leu Val Asp Val Pro Lys
                245             250             255

Asp Ile Gln Gln Gln Leu Ala Ile Pro Asn Trp Glu Gln Ala Met Arg
            260             265             270

Leu Pro Gly Tyr Met Ser Arg Met Pro Lys Pro Pro Glu Asp Ser His
        275             280             285

Leu Glu Gln Ile Val Arg Leu Ile Ser Glu Ser Lys Lys Pro Val Leu
    290             295             300

Tyr Val Gly Gly Gly Cys Leu Asn Ser Ser Asp Glu Leu Gly Arg Phe
305             310             315             320

Val Glu Leu Thr Gly Ile Pro Val Ala Ser Thr Leu Met Gly Leu Gly
                325             330             335

Ser Tyr Pro Cys Asp Asp Glu Leu Ser Leu His Met Leu Gly Met His
            340             345             350

Gly Thr Val Tyr Ala Asn Tyr Ala Val Glu His Ser Asp Leu Leu Leu
        355             360             365

Ala Phe Gly Val Arg Phe Asp Asp Arg Val Thr Gly Lys Leu Glu Ala
    370             375             380

Phe Ala Ser Arg Ala Lys Ile Val His Ile Asp Ile Asp Ser Ala Glu
385             390             395             400

Ile Gly Lys Asn Lys Thr Pro His Val Ser Val Cys Gly Asp Val Lys
                405             410             415
```

```
Leu Ala Leu Gln Gly Met Asn Lys Val Leu Glu Asn Arg Ala Glu Glu
            420                 425                 430

Leu Lys Leu Asp Phe Gly Val Trp Arg Asn Glu Leu Asn Val Gln Lys
        435                 440                 445

Gln Lys Phe Pro Leu Ser Phe Lys Thr Phe Gly Glu Ala Ile Pro Pro
    450                 455                 460

Gln Tyr Ala Ile Lys Val Leu Asp Glu Leu Thr Asp Gly Lys Ala Ile
465                 470                 475                 480

Ile Ser Thr Gly Val Gly Gln His Gln Met Trp Ala Ala Gln Phe Tyr
                485                 490                 495

Asn Tyr Lys Lys Pro Arg Gln Trp Leu Ser Ser Gly Leu Gly Ala
            500                 505                 510

Met Gly Phe Gly Leu Pro Ala Ala Ile Gly Ala Ser Val Ala Asn Pro
        515                 520                 525

Asp Ala Ile Val Val Asp Ile Asp Gly Asp Gly Ser Phe Ile Met Asn
        530                 535                 540

Val Gln Glu Leu Ala Thr Ile Arg Val Glu Asn Leu Pro Val Lys Val
545                 550                 555                 560

Leu Leu Leu Asn Asn Gln His Leu Gly Met Val Met Gln Trp Glu Asp
            565                 570                 575

Arg Phe Tyr Lys Ala Asn Arg Ala His Thr Phe Leu Gly Asp Pro Ala
            580                 585                 590

Gln Glu Asp Glu Ile Phe Pro Asn Met Leu Leu Phe Ala Ala Ala Cys
        595                 600                 605

Gly Ile Pro Ala Ala Arg Val Thr Lys Lys Ala Asp Leu Arg Glu Ala
    610                 615                 620

Ile Gln Thr Met Leu Asp Thr Pro Gly Pro Tyr Leu Leu Asp Val Ile
625                 630                 635                 640

Cys Pro His Gln Glu His Val Leu Pro Met Ile Pro Ser Gly Gly Thr
            645                 650                 655

Phe Asn Asp Val Ile Thr Glu Gly Asp Gly Arg Ile Lys
            660                 665
```

EFFECTS OF A PLURALITY OF MUTATIONS TO IMPROVE HERBICIDE RESISTANCE/TOLERANCE IN RICE

CROSS REFERENCE TO RELATED APPLICATIONS

The application claims the benefit of priority under 35 U.S.C. § 119(e) to U.S. Provisional Application No. 62/452,800, filed Jan. 31, 2017, U.S. Provisional Application No. 62/453,094, filed Feb. 1, 2017, U.S. Provisional Application No. 62/508,264, filed May 18, 2017, and U.S. Provisional Application No. 62/573,451, filed Oct. 17, 2017. The disclosures set forth in the referenced applications are incorporated herein by reference in their entireties.

BACKGROUND

Sequence Listing

The instant application contains a Sequence Listing which has been submitted electronically in ASCII format and is hereby incorporated by reference in its entirety. Said ASCII copy, created on Dec. 27, 2017, is named 269608_SEQ_ST25.txt and is 65,409 bytes in size.

Mutant rice is disclosed that is (1) resistant/tolerant to AHAS/ALS inhibitors especially imidazolinone ("IMI") herbicides, at a relatively high concentration of inhibitors, and (2) wherein the mutations effect synergistic responses in rice to the herbicides. Methods of weed control are disclosed using herbicide resistant/tolerant rice with these mutations as crops in fields. Methods to produce herbicide resistant/tolerant rice are also disclosed.

Improving Value of Rice Crops

Rice is an ancient agricultural crop and today is one of the principal food crops of the world. There are two cultivated species of rice: *Oryza sativa* L., the Asian rice, and *Oryza glaberrima* Steud, the African rice. The Asian species constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valley of California. Other countries, in particular in South America and the East, are major rice producers.

Rice is one of the few crops that can be grown in a shallow flood as it has a unique structure allowing gas exchange through the stems between the roots and the atmosphere. Growth in a shallow flood results in the best yields and is the reason that rice is usually gown in heavy clay soils, or soils with an impermeable hard pan layer just below the soil surface. These soil types are usually either not suitable for other crops or at best, the crops yield poorly.

The constant improvement of rice is imperative to provide necessary nutrition for a growing world population. A large portion of the world population consumes rice as their primary source of nutrition, and crops must thrive in various environmental conditions including competing with weeds and attacks by unfavorable agents. Rice improvement is carried out through conventional breeding practices and also by recombinant genetic techniques. Though appearing straightforward to those outside this discipline, crop improvement requires keen scientific and artistic skill and results are generally unpredictable.

Although specific breeding objectives vary somewhat in the different rice producing regions of the world, increasing yield is a primary objective in all programs.

Plant breeding begins with the analysis and definition of strengths and weaknesses of cultivars in existence, followed by the establishment of program goals to improve areas of weakness to produce new cultivars. Specific breeding objectives include combining in a single cultivar an improved combination of desirable traits from the parental sources. Desirable traits may be introduced due to spontaneous or induced mutations. Desirable traits include higher yield, resistance to environmental stress, diseases, and insects, better stems and roots, tolerance to low temperatures, better agronomic characteristics, nutritional value and grain quality.

For example, the breeder initially selects and crosses two or more parental lines, followed by selection for desired traits among the many new genetic combinations. The breeder can theoretically generate billions of new and different genetic combinations via crossing. Breeding by using crossing and selfing, does not imply direct control at the cellular level. However, that type of control may be achieved in part using recombinant genetic techniques.

Pedigree breeding is used commonly for the improvement of self-pollinating crops such as rice. For example, two parents which possess favorable, complementary traits are crossed to produce an $F_1$ generation. One or both parents may themselves represent an $F_1$ from a previous cross. Subsequently a segregating population is produced, by growing the seeds resulting from selfing one or several $F_1$s if the two parents are pure lines, or by directly growing the seed resulting from the initial cross if at least one of the parents is an $F_1$. Selection of the best individual genomes may begin in the first segregating population or $F_2$; then, beginning in the $F_3$, the best individuals in the best families are selected. "Best" is defined according to the goals of a particular breeding program e.g., to increase yield, resist diseases. Overall a multifactorial approach is used to define "best" because of genetic interactions. A desirable gene in one genetic background may differ in a different background. In addition, introduction of the gene may disrupt other favorable genetic characteristics. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new parental lines.

Backcross breeding has been used to transfer genes for a highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the desired phenotype of the donor parent are selected and repeatedly crossed (backcrossed) to the recurrent parent. The process is used to recover all of the beneficial characteristics of the recurrent parent with the addition of the new trait provided by the donor parent.

Promising advanced breeding lines are thoroughly tested and compared to appropriate standards in environments representative of the commercial target area(s) for at least three or more years. The best lines are candidates for new commercial varieties or parents of hybrids; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is not only a time-consuming process, but requires precise forward planning, efficient use of resources, and a minimum of changes in direction. The results include novel genetic combinations not found in nature.

Some improvement of rice through breeding may be restricted to the natural genetic variation in rice and hybridizing species, such as wild rice. The introduction of new variation in a breeding program is usually through the crossing program as described, such as pedigree or backcross breeding. However, occasionally natural mutations are found that result in the introduction of new traits such as disease resistance or height changes. Breeders have also developed new traits by inducing mutations (small changes in the DNA sequence) into a rice genome. Some of these mutations or combination of genes are not found in nature. Commonly, EMS (Ethyl methanesulfonate) or sodium azide plus MNU (N-methyl-N-nitrosourea) are used as mutagenic agents. These chemicals randomly induce single base changes in DNA, usually of G and C changed to A and T. Overall effects are unpredictable. Most of these changes have no effect on the crop, because they fall either outside the gene coding regions or do not change the amino acid sequence of the gene product. However, some produce new traits or incorporate new DNA changes into previous lines.

The breeder has no direct control of mutation sites in the DNA sequence. The identification of useful changes is usually due to the random possibility that an effective mutation will be induced, and that the breeder will recognize the phenotypic effects of the change and will be able to select rice having that mutation for production. Seeds are treated with a mutagenic chemical and immediately planted to grow. The resulting plants are designated as M0 as the starting mutagenized population. M0, screened or not, can be selfed in autogamous crops like rice to produce M1 progeny, and subsequently M2, M3, and so forth, as the population is advanced. The M2 seed will carry numerous new variations; therefore, no two experiments will produce the same combinations. Among these variations new traits previously not existing in rice and previously unavailable for selection by a plant breeder may be found and used for rice improvement.

To find new traits the breeder must use efficient and targeted selection strategies because the process is completely random and has an extremely low frequency of useful new combinations. Among thousands of induced new genetic variants, there may be only one with a desirable new trait. An optimal selection system will screen through thousands of new variants and allow detection of a few or even a single plant that might carry a new trait. After identifying or finding a possible new trait, the breeder must develop a new cultivar by pedigree or backcross breeding and extensive testing to verify the new trait and cultivar exhibits stable and heritable value to rice producers. After a mutation is identified by whatever means, it may be transferred into rice by recombinant techniques.

Herbicide Resistance in Rice

Weeds in crop fields compete for resources and greatly reduce the yield and quality of the crop. Weeds have been controlled in crops through the application of selective herbicides that kill the weeds, but do not harm the crop. Usually selectivity of the herbicides is based on biochemical variations or differences between the crop and the weeds. Some herbicides are non-selective, meaning they kill all or almost all plants. Non-selective or broad spectrum herbicides can be used in crops only if the crops have a genetic mechanism that confers tolerance to the herbicides. Crops can be converted into "Herbicide Tolerance" (HT) if new genes are inserted that express specific proteins that convey tolerance or resistance to the herbicide. Resistance to herbicides has also been achieved in crops through genetic mutations that alter proteins and biochemical processes. These mutations may arise in nature, but in most crops identified they have been effected by the breeder.

In some instances, especially with repeated use of a particular herbicide, weeds have developed resistance through the unintended selection of natural mutations that provide resistance. When weeds become resistant to a particular herbicide, that herbicide is no longer useful for weed control. The development of resistance in weeds may be delayed through alternating the use of herbicides with different modes of action to control weeds, interrupting development of resistant weeds.

Rice production is plagued by broad leaf and grass weeds that are difficult to control, amongst which there is a particularly hard to control weed called "red rice". One difficulty arises because red rice is so genetically similar to cultivated rice (they occasionally cross pollinate) that there are no selective herbicides available that target red rice, yet do not harm the cultivated rice. Control is currently provided in commercial rice production through the development of mutations found in rice that render rice resistant to broad spectrum herbicides e.g. imidazolinone and sulfonylurea herbicides. Rice crops resistant to herbicides that inhibit other deleterious plants, such as broad leaf plants, are needed.

Finding new mutations in rice that improve resistance to herbicides, would greatly benefit rice production. Obtaining and incorporating genes and combination of genes for improved herbicide resistance into rice genomes, while maintaining favorable characteristics to maintain or improve fitness, is challenging, unpredictable, time consuming and expensive, but necessary to meet the world's increasing food needs.

SUMMARY

Described and disclosed herein are novel and distinctive rice lines and hybrids with unique resistances to herbicides, in particular AHAS/ALS inhibiting herbicides.[1] The resistance conferred to rice plants by the substitutions A205V/G6254E in the AHAS/ALS amino acid sequence, when the rice plants are challenged by IMI herbicides, is significantly higher than that resistance/tolerance shown by a rice plant carrying A205V alone or G654E alone. The uniqueness is due to a combination of genetic mutations leading to synergistic increases in herbicide tolerance/resistance in rice with the combination of genetic mutations, compared to levels of tolerance/resistance caused by the individual genetic mutations.

[1]For names of some suitable "IMI" herbicides, see "DEFINITIONS."

Various mutations in the nucleic acid coding sequence for the AHAS/ALS[2] enzyme cause amino acid substitutions that when expressed in rice result in an enzyme resistant to IMI tolerant herbicides. FIG. 1 shows alignment of nucleic acid sequences that encode amino acid sequences of AHAS/ALS in 2 rice lines, one (0001-2-2) with a mutation causing substitution A205V and another (80034-5) ≠[2]The gene coding for the acetohydroxyacid synthase protein (AHAS, EC2.2.1.6), also referred to as acetolactate synthase (ALS)

in rice is present at a single locus in rice listed at locus LOC_Os06g51280 in the annotated database. causing substitution G654E. Also shown are sequences in wild type rice (P1003) and R0146, a parental proprietary line. The designated amino acid substitutions encoded, are listed in boxes underneath the mutated codons. FIG. 2 shows positions of some of the AHAS/ALS known amino acid substitutions [205 (179), 653 (627), 654 (628)].[3]

[3] Using both the Blackgrass and rice position numbers.

Stacking of both genetic mutations (designated RTC1 and RTC2)[4] is exemplified by the genomes of seeds from three hybrids deposited under the Budapest Treaty and designated in the ATCC as PTA-123859, PTA-123860, and PTA-123861 respectively (See Table 1).

[4] RTC1 caused the A205V amino acid substitution in the AHAS/ALS enzyme, wherein valine replaces alanine, and RTC2 caused the G654E substitution, wherein glutamic acid replaces glycine.

Unexpectedly, synergism exhibited in terms of IMI herbicide tolerance, is clearly greater than the sum of the dose/tolerance manifested by the AHAS protein carrying a single A205V or a single G654E mutation. Using data from multiple experiments, (identified as 15SA-T11, 16-T7, 16GH-T7) conducted over 2 years, in multiple locations, with multiple different imidazolinone herbicides (imazetaphyr, imazamox and imazetapic) and multiple lines, it was estimated that the specific interaction of the two single mutations RTC1+RTC2, when acting together (RTC1-RTC2), and expressed as the additional avoidance of % Injury relative to the individual mutations, can be estimated as −25% reduction of rate of injury at doses of 1×, −55% reduction in injury at 2×, −65% at 3× and −67% reduction at 4× (FIG. 10A).

It is a surprising and unexpected result to find herbicide resistance/tolerance affected by a combination of mutations leading to two different substitutions in a target enzyme, as disclosed herein, AHAS/ALS. It is particularly unexpected that the combination produces a synergistic response—less percent injury due to herbicide exposure in rice with the combination, than in rice with either mutation alone. Importantly, yield was not deleteriously affected, as has been reported attending some mutant herbicide resistant/tolerant rice.

Because these mutations affect the same enzyme and are in the same gene, one might have expected at most an additive effect, and likely a negative effect on the enzyme. Unexpectedly, synergism in the level of herbicide tolerance resulted, without deleterious effects on other traits (Tables 3, 4).

The mechanism of herbicide tolerance has been classified roughly into two groups: target-site and non-target-site herbicide tolerance. Target-site herbicide tolerance is caused by the prevention of herbicide binding to the target enzyme, caused by point mutations occurring in the target. The molecular mechanisms of target-site herbicide tolerance are regulated mostly by a single gene encoding a target enzyme harboring a point mutation. The hybrids disclosed herein, have a combination of 2 point mutations.

Disclosed herein is a method to control weeds in a rice field, wherein the rice in the field includes plants resistant to IMI herbicides. The method includes:
  a. using herbicide resistant/tolerant rice in the field; and
  b. contacting the rice field with at least one herbicide, or a plurality of herbicides, for example, any that may belong to the family of chemicals known as AHAS/ALS-inhibitors, or any that may belong to the class of herbicides known as AHAS/ALS-inhibiting herbicides.

A method for growing herbicide resistant/tolerant rice plants includes (a) planting resistant rice seeds; (b) allowing the rice seeds to sprout; (c) applying one or more herbicides to the rice sprouts at levels of herbicide that would normally inhibit the growth of a rice plant.

Methods of producing herbicide-tolerant rice plants may also use a transgene or plurality of transgenes. One embodiment of such a method is transforming a cell of a rice plant with transgenes, wherein the transgenes encode 2 different mutations each leading to rice resistant to IMI inhibitors. Any suitable cell may be used in the practice of these methods, for example, the cell may be in the form of a callus. Specific mutations disclosed herein include those leading to substitutions A205V and G654E in the AHAS/ALS enzyme. With this combination, synergism in resistance was effected.

BRIEF DESCRIPTION OF DRAWINGS

The patent or application file contains at least one drawing executed in color. Copies of this patent or patent application publication with color drawing(s) will be provided by the office upon request and payment of the necessary fee.

FIG. 2 also discloses SEQ ID NOS: 8-9, respectively, in order of appearance (Cyp-MT-653, Cyp-WT). Blanks show non-alignment.

FIG. 3A to FIG. 3I illustrate the results of Example 1: FIG. 3A control; FIG. 3B 0.5× Imazamox; FIG. 3C 1× Imazamox; FIG. 3D 2× Imazamox; FIG. 3E 4× Imazamox; FIG. 3F 1× Imazethapyr+0.5× Imazamox; FIG. 3G 1× Imazethapyr+1× Imazamox; FIG. 3H 1× Imazethapyr+2× Imazamox; FIG. 3I 1× Imazethapyr+4× Imazamox; Pots L to R: LF2-RTC2/LM1-RTC1, LF1-RTC2/LM1-RTC1, LF3-RTC2\LM4-RTC1, mutated line P1003A205V, mutated line R0146G654E, sensitive control commercial variety Cypress, commercial hybrid CLXL745.

FIG. 4 graphically illustrates the results of Example 1.

FIG. 5A; Control; FIG. 5B 8×; FIG. 5C 1×; FIG. 5D; 0.25×; Planting order L to R: P1003A205V, R0146G654E, P1003, LF2-RTC2/LM1-RTC1, LF3-RTC2\LM4-RTC1.

FIG. 8 is a graphical illustration of percent injury 4 weeks post preflood application.

RTC2% Injury calculated as [(RTC1+RTC2)−(RTC1XRTC2/100)]; FIG. 10A shows average % injury 3 weeks post herbicide application and RTC1−RTC2 synergistic effects calculated as stated above; FIG. 10B graphically shows percent average % injury, at different application doses, for the homozygous single mutation lines, RTC1 and RTC2, and the double hemizygous RTC1/RTC2.

DETAILED DESCRIPTION

Figure 1:
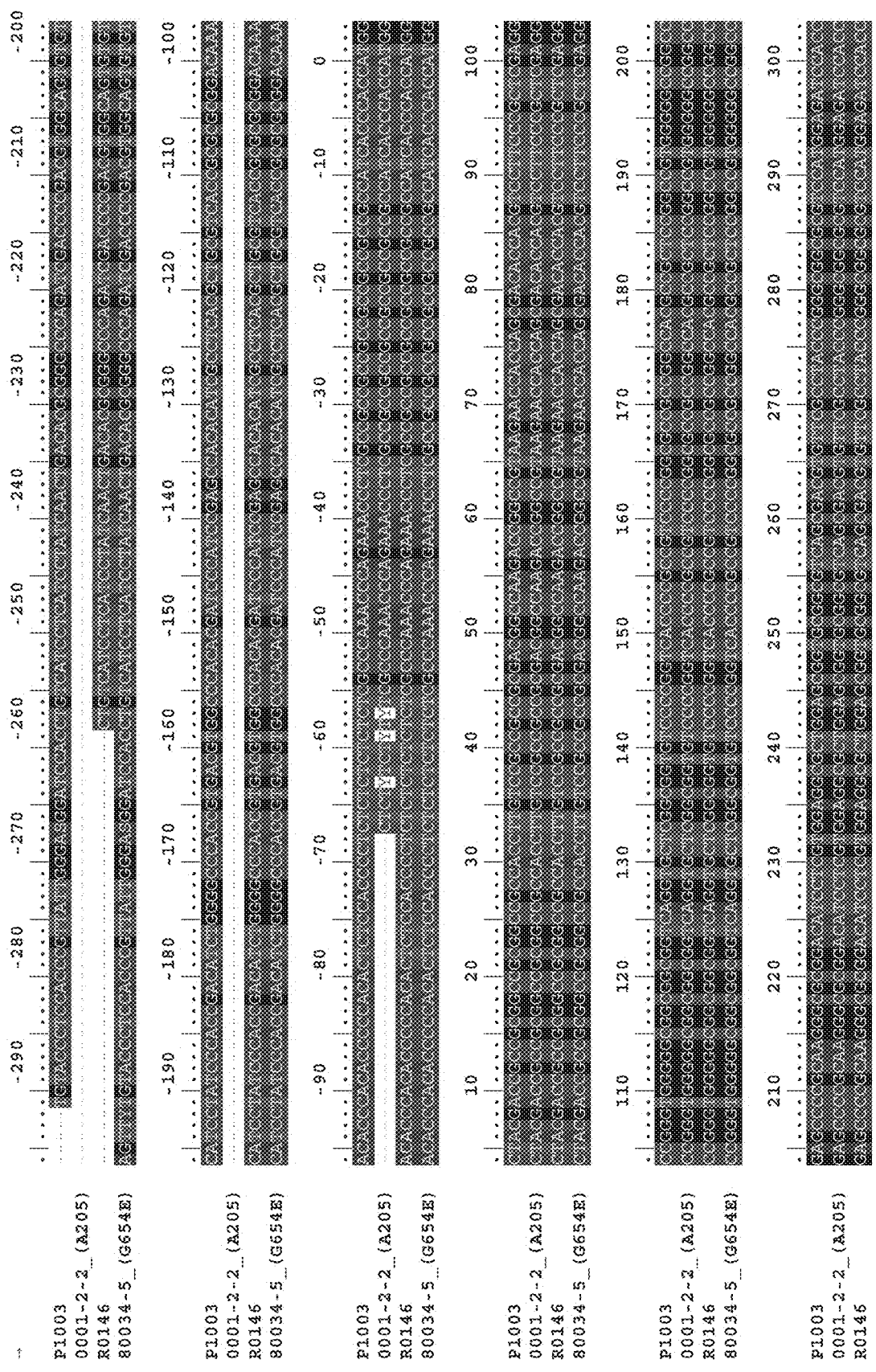
FIG. 1 shows an alignment of nucleic acid sequences among wild type rice line P1003 (SEQ ID NO: 1), proprietary parental line R0146 (SEQ ID NO: 3), and one line that has a mutation encoding a substitution A205 (179)V (SEQ ID NO: 2) and another line with G654 (628)E (SEQ ID NO: 4).
Figure 1:
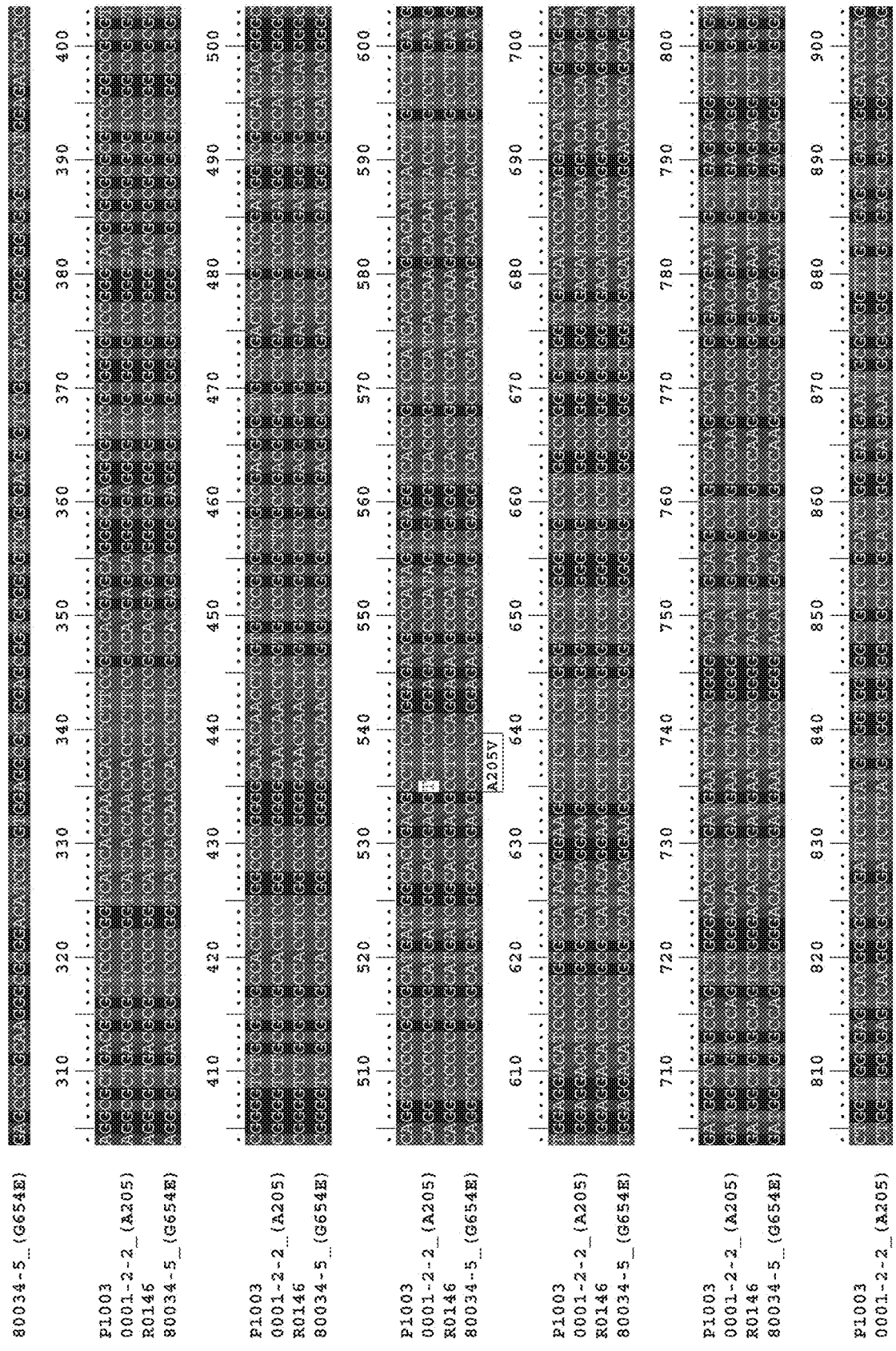
Figure 1:
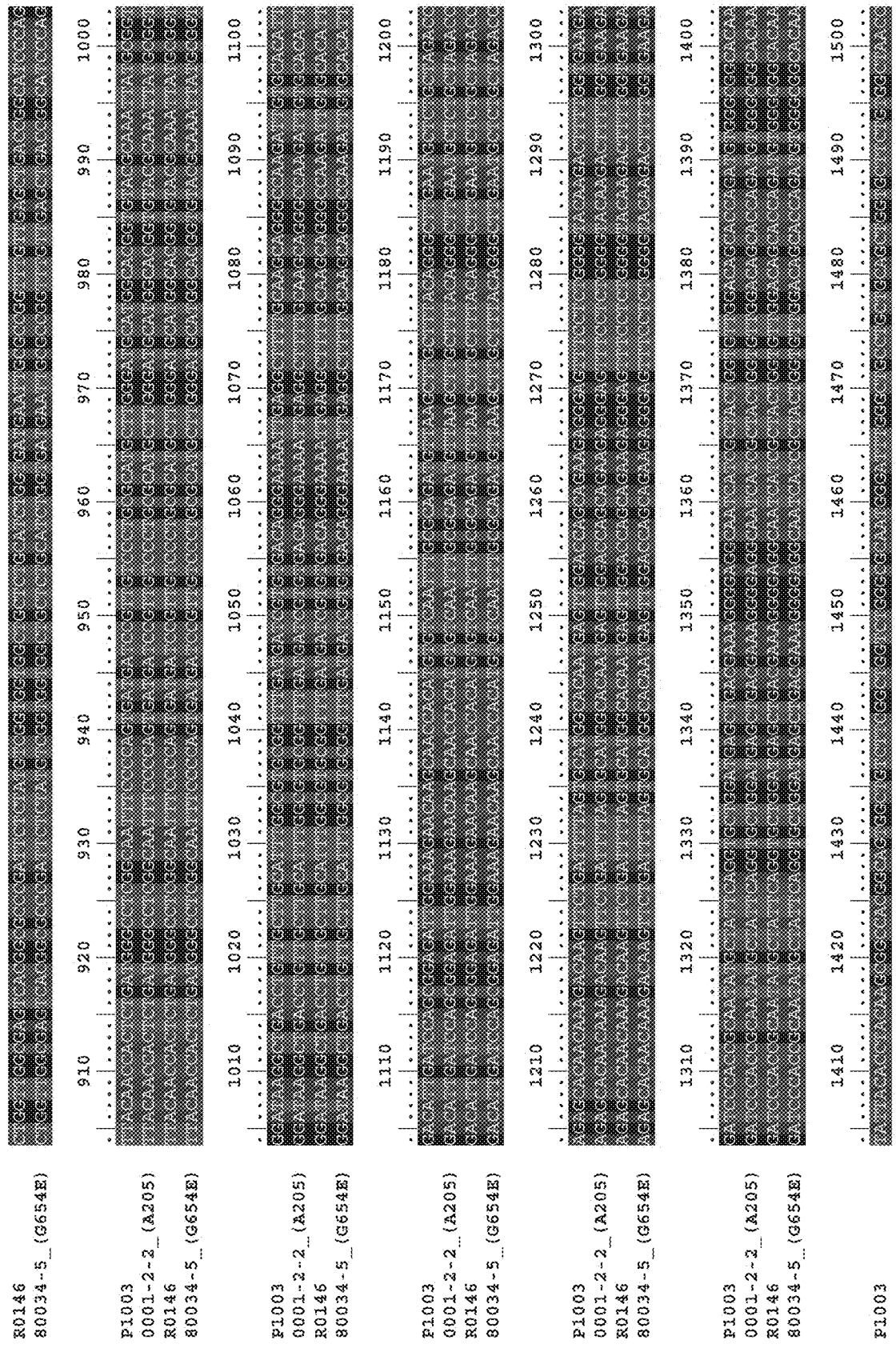
Figure 1:
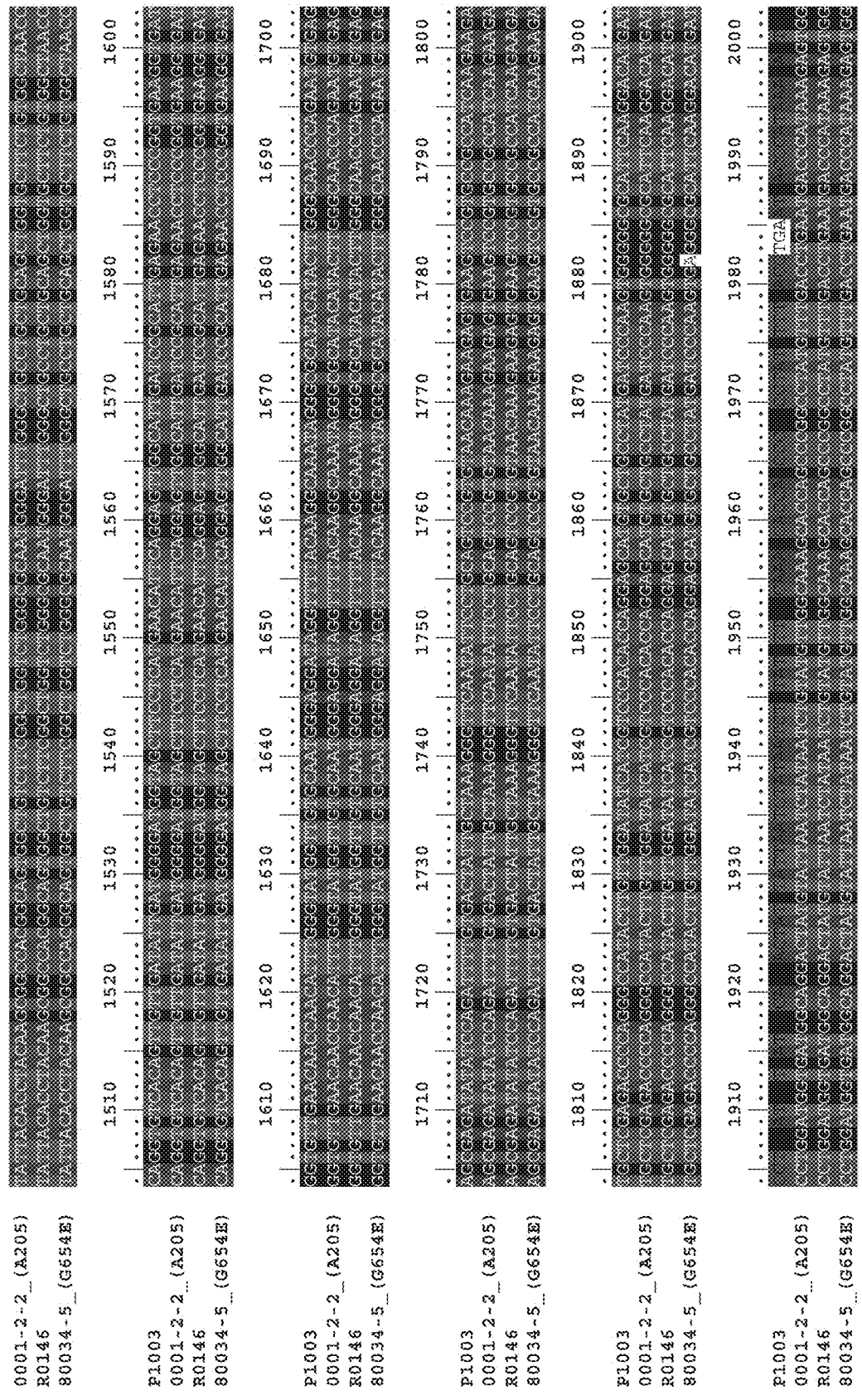
Figure 1:
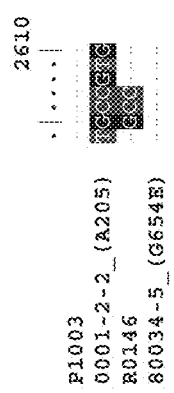
Figure 2:
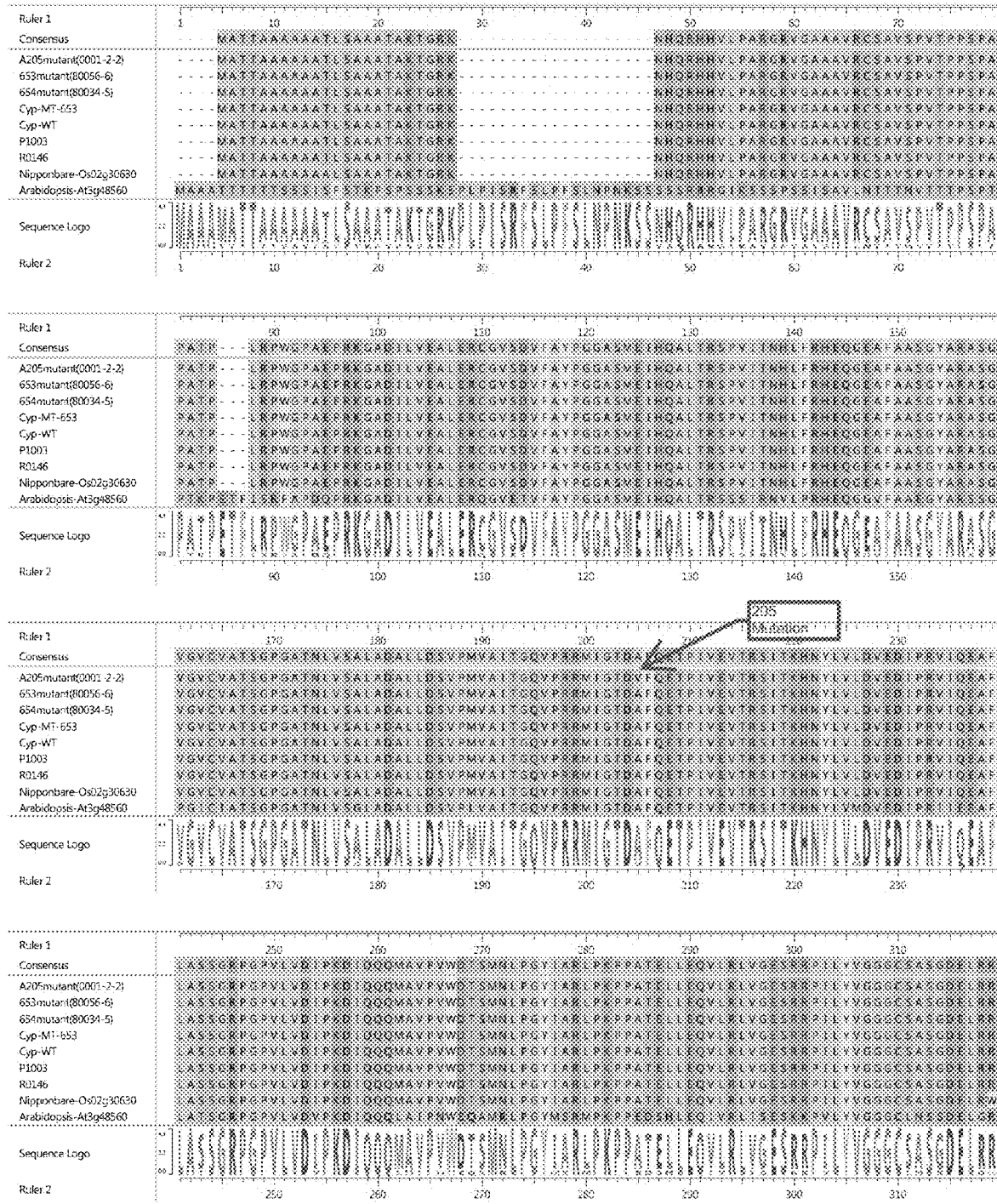
FIG. 2 shows the AHAS/ALS amino acid sequence alignment of substitutions at positions 205 (SEQ ID NO: 5), 653 (SEQ ID NO: 6) and 654 (SEQ ID NO: 7); where P1003 (SEQ ID NO: 10) and R0146 (SEQ ID NO: 11) are unmutated rice lines; also shown are Nipponbare (SEQ ID NO: 12) and *Arabidopsis* (SEQ ID NO: 13).
Figure 2:
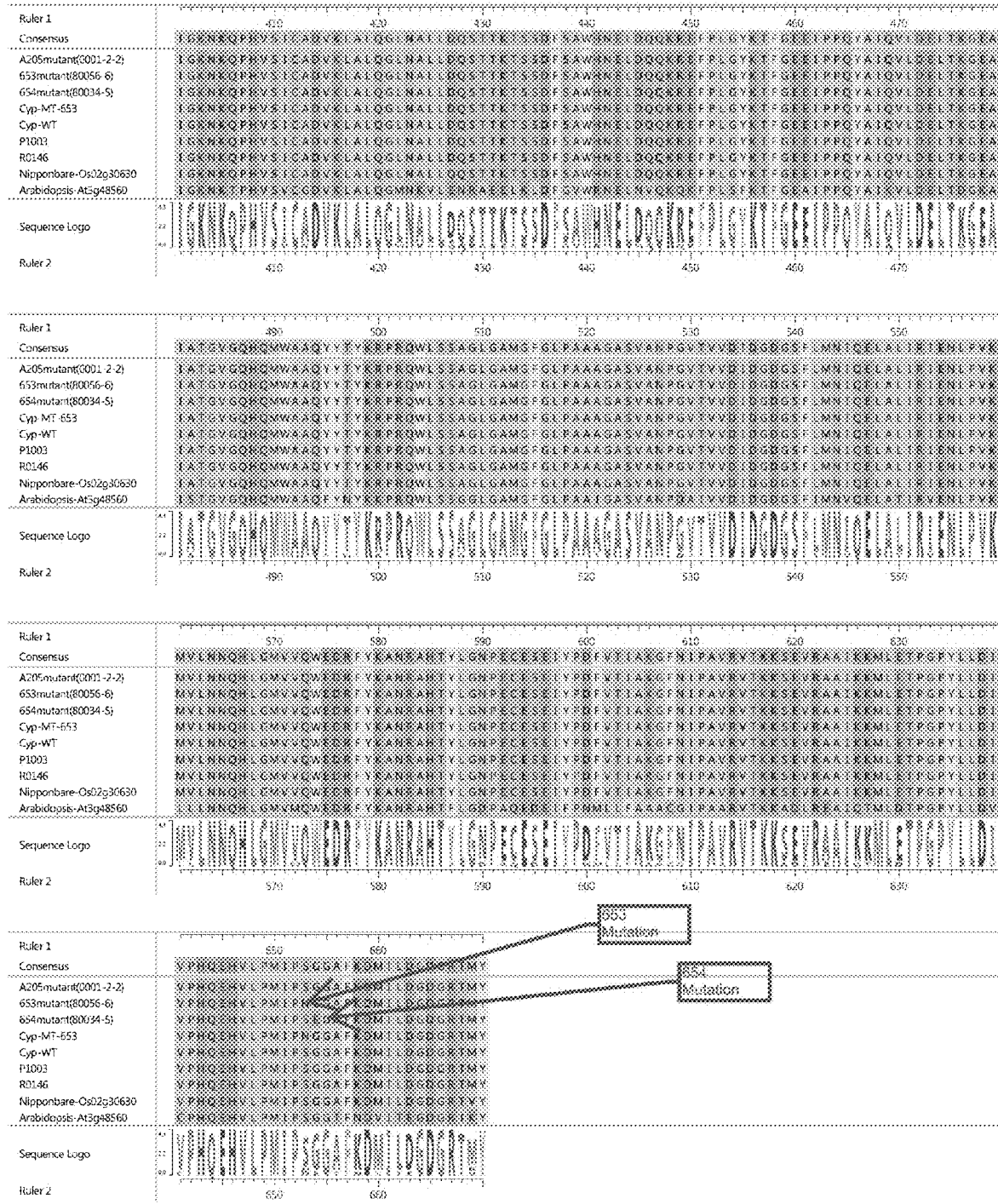

Rice lines having different herbicide resistance genes, either pyramided or stacked in the same genetic background or, as single products that are used alternatively in the rotation used by the farmer, represent a critical tool or strategy in extending the useful life of herbicides because these practices slow the development of herbicide resistant variants among the targeted weeds. Several methods are possible to deploy these resistances into hybrids or varieties for weed control, as well as options for hybrid seed production. The rice lines described herein represent new methods for weed control in rice and can be deployed in any of many possible strategies to control weeds and provide for long-term use of these and other weed control methods.

The Novel Effect of Dual Mutations on the AHAS Protein

AHAS is an important enzyme in plants and microorganisms that catalyzes the formation of acetolactate from pyruvate, the first step in the biosynthesis of aminoacids valine and isoleucine. The functional protein complex can have a homodimer or homotetramer structure, and presents both large catalytic subunits and small regulatory subunits.

The regulatory subunit stimulates activity of the catalytic subunit and confers sensitivity to feedback inhibition by branched-chain amino acids. Because the AHAS crystalline structure is well characterized for *Arabidopsis thaliana*, it has been possible to (1) identify the AHAS-herbicide binding sites (2) establish and understand the molecular interaction between AHAS, its cofactors and the herbicides that affect it. The AHAS catalytic site is deep within a channel of the protein, but it is noteworthy that AHAS herbicides do not bind within the catalytic site. Rather, they bind across an herbicide binding domain that straddles the channel entry, thereby blocking substrate access to the catalytic site and interrupting normal enzyme metabolism causing death to the plant. Across this domain, many amino acid residues are involved in herbicide binding. Structurally different AHAS herbicides orientate differently in the herbicide binding domain, causing a variable level of interaction for any given substitution. Specific amino acid substitutions within the herbicide binding domain can confer resistance to some, but not to other, AHAS herbicides (see review in Powles and Yu, 2010).

Despite the large number of well characterized single induced or spontaneous mutations across many of the amino acid residues, none have been reported describing simultaneous substitutions at 2 or more active substitutions at critical amino acid residues of the AHAS gene. Also, given the proximity of these different active herbicide binding sites, it is also impossible to stack these from single mutation donors into a single background genome, by means of sexual reproduction. This limitation exists simply on account of the extraordinary improbability of such a specific recombination event. Thus, the novelty of the RTC1−RTC2 product which effectively overcomes the otherwise improbable combination of multiple mutations in the AHAS protein, in hybrid rice disclosed herein. The hybrids were produced by combining the two different mutated alleles at the AHAS locus, which in turn, produces a functional protein complex that contains subcomponents of both forms. Surprisingly the result is to confer on the rice, synergistic herbicide tolerance when compared with the pure form single mutation effects.

Applications of Rice with 2 Different Mutations

Cells derived from herbicide resistant seeds, plants grown from such seeds and cells derived from such plants, progeny of plants grown from such seed and cells derived from such progeny are within the scope of this disclosure. The growth of plants produced from deposited seeds, and progeny of such plants will typically be resistant/tolerant to herbicides, e.g. an IMI inhibitor at levels of herbicides that would normally inhibit the growth of a corresponding wild-type plant. There are some natural (non-induced) levels of tolerance to some herbicides, but they are not capable of protecting plants at levels that would be commercially useful.

A method for controlling growth of weeds in the vicinity of herbicide resistant/tolerant rice plants is also within the scope of the disclosure. One example of such methods is applying one or more herbicides to the fields of rice plants at levels of herbicide that would normally inhibit the growth of a rice plant. For example, at least one herbicide inhibits AHAS/ALS activity.

In order to maximize weed control in a rice field, different herbicides may be required to cover the spectrum of weeds present and, in turn, several applications along the crop cycle may be required for any one particular herbicide depending on the overlap between the window of effective control provided by a single application and the window of time during which its target weed may germinate, which often is longer than the protection afforded by a single herbicide application. Temperature, and soil moisture conditions are key factors that affect both window of herbicide efficacy, window of moment of weed germination and growth. Based on these factors, herbicide control models often include sequential repeated application during the crop cycle.

In a standard herbicide tolerance system, for example, one currently used commercially in rice, for resistance to imidazolinone herbicides, the first application of the herbicide is applied at the 2 leaf stage, with the second application following a minimum of 10 days later just prior to the establishment of permanent flood when the plants are tillering. The purpose of the second application is to eliminate weeds that may have germinated after the first application before they can be effectively suppressed by flooding. In some traits, including "IMI" inhibitor herbicides, the timing of herbicide applications can be critical not only for effective weed control, but also for the level of tolerance observed in the plants themselves. Plant injury observed in response to herbicide application may align closely with plant stage. In some rise lines, very early post-emergence applications cause much higher injury at the 1 leaf stage, with observed injury declining at each growth stage of the plant through first tiller. Some herbicide tolerance traits even exhibit no tolerance to pre-emergent applications even though post-emergence tolerance is excellent. This variable herbicide response linked to plant growth stage requires careful testing to establish the boundaries of safe usage of a new herbicide tolerant product.

A plurality includes, for example, at least 2 "IMI" herbicides.

In considering combinations of different herbicide resistance genes, irrespective of whether the combination includes two or more different modes of action for the same herbicide, or two or more genes for herbicides of different families or functions, antagonistic or synergistic interactions may be observed resulting from gene to gene interactions, as some of the embodiments described herein have evidenced. The combination disclosed herein of the novel mutated genes resistant to AHAS/ALS-inhibiting herbicides results in herbicide tolerance that is far superior to the additive resistance of the two genes acting individually, demonstrating synergism. (FIGS. 3-6; Examples 1-4).

Figure 11:
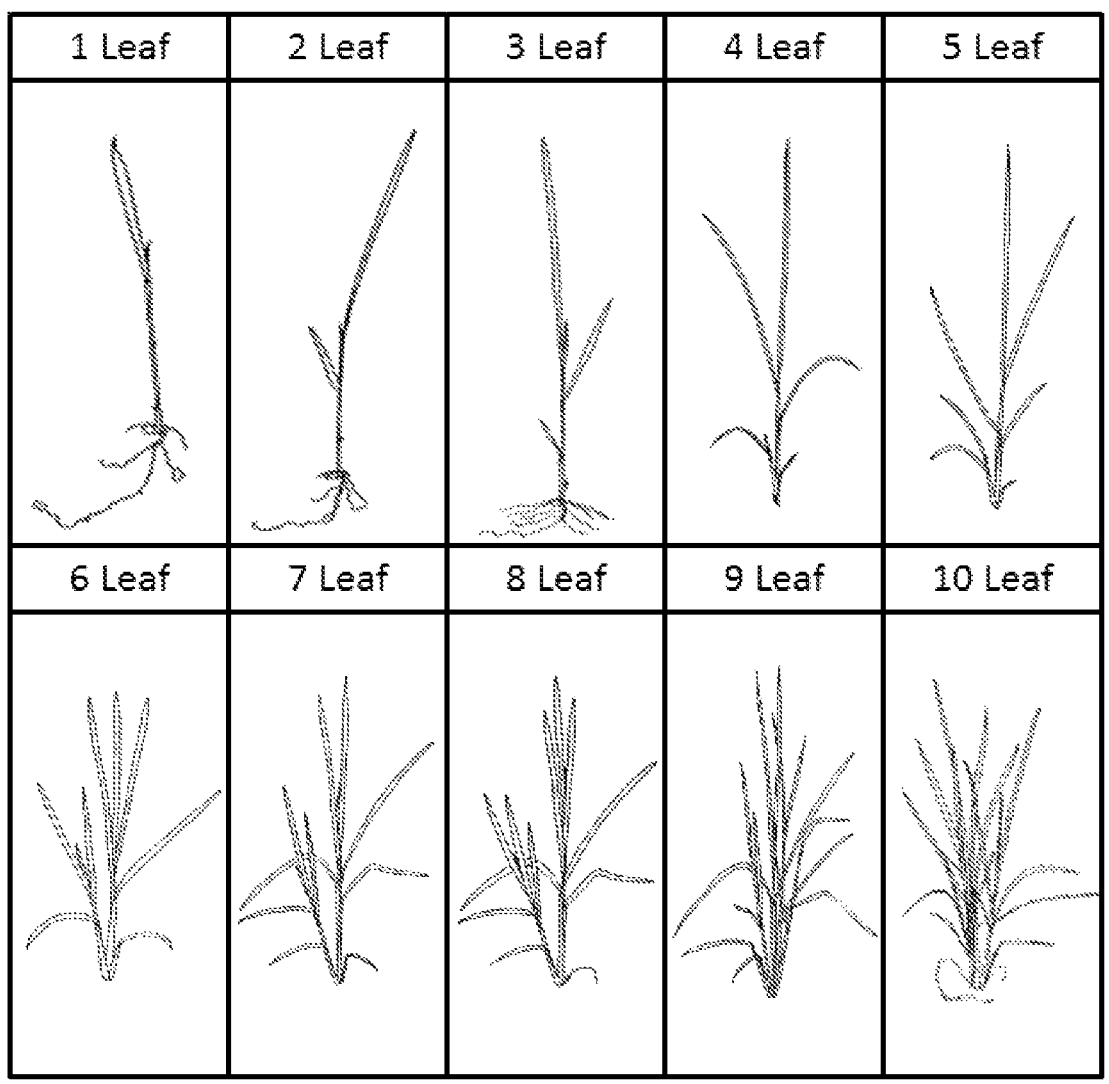
FIG. 11 shows developmental stages of rice.

Rice production for good yields requires specific weed control practices. Some herbicides are applied as premergents, after planting but before crop emergence; other as postemergents. In the case of rice, postemergent application can be before the crops are flooded, of after. Preferred applications are normally times, according to the developmental stage of the crop, as defined by the number of open leaves in the growing plant (FIG. 11: Developmental Stages of Rice). Timing of herbicide applications is an important factor, not only from the perspective of maximizing the efficiency of weed control, but also from the perspective of minimizing impact on the herbicide tolerant crop. This consideration stems from the fact that mutagenized, naturally occurring or transgenic herbicide resistances often are not completely independent of dose and application timing effects. Different genes of herbicide resistance have different dose responses, as well as timing of application responses whereby, typically, phytotoxity in the resistant crop increases as dose increases beyond a certain level, or phytotoxicity to the resistant crop varies with varying timings of application for a given herbicide dose.

Evaluation of the novel herbicide resistance genes, subject of this application, was conducted with a range of suitable herbicide doses, that cover application rates typically used for rice farming operations while also taking into consideration possible deviations from the manufacturer-recommended doses. Considering 1×, the recommended manufacturers or best practice recommended dose, the most frequently evaluated additional doses are 2× and 4× with some experiments including other values.

The RTC1 line was derived from rice line P1003. RTC2 was derived from R0146—a proprietary line of Chinese origin. Neither of these two lines has any tolerance to imidazolinone herbicides. After backcrossing to fix the mutations and remove unwanted effects, the traits have been introgressed into a number of inbred rice lines in order to produce a range of hybrid rice varieties suited to a range of different commercial requirements for herbicide tolerance.

The A179(205)V mutation was developed by EMS mutagenesis from the line P1003, also called Lemont, which is the public variety designated Cypress. The independently developed mutation G628(654)E was obtained by chemical mutagenesis process (Sodium Azide+MNU) from the proprietary line R0146 of Chinese origin. These mutations were independently fixed by inbreeding during the line optimization process following the mutagenesis and early detection, and are therefore available in stable homozygous configuration in the derived inbred lines. These two independent mutations, being localized in the same expressed gene at positions contained within the same protein, are not stacked in an inbred stock. Fortunately, hybrid products with one dose of each allele and expressing both modifications show higher herbicide tolerance than homozygous lines for either gene and are, therefore, the targeted product.

All genetic materials used in the development of these mutants, or derived therein, are the property of RiceTec. All markers used were internally developed from available public sequences or from sequence information derived from the same materials. Standard IMI commercial herbicides were selected for the screening process, using label guidance to determine herbicide use parameters. Herbicide response was determined using plant injury rates (See TABLE 2).

TABLE 3 is a comparison of morphological-physiological/grain quality attributes of the RTC1-RTC2 hybrid rice lines, compared to their non-mutated counterparts, to highlight that these mutant IMI tolerant rice lines are otherwise agronomically identical to their non-mutated counterparts. Overall, there were no commercially relevant differences identified between the RTC1-RTC2 rice hybrids and their un-mutated controls (same original line lacking the mutations). Comparison of hybrids containing both mutations with the single mutation and with the control line also showed few statistically significant differences, none of which are biologically relevant. It is known that mutagenic treatments often result in multiple changes in the regenerated plants, but these lines have been repeatedly backcrossed and converted into inbred lines thereby removing unwanted mutations from the germplasm.

The examples below are illustrative of the invention, but not limiting.

EXAMPLES

Example 1: 16GH-T7: Imazamox Trial (See FIG. 3A to FIG. 3I and FIG. 4)

FIG. 3 Trial Setup:
Trial consisted of 2 treatment regimens with Imazamox applications at approximately the preflood stage with rates of 0.5×, 1×, 2×, or 4×, either alone or 2 weeks following application of 1× Imazethapyr.

Figure 4:
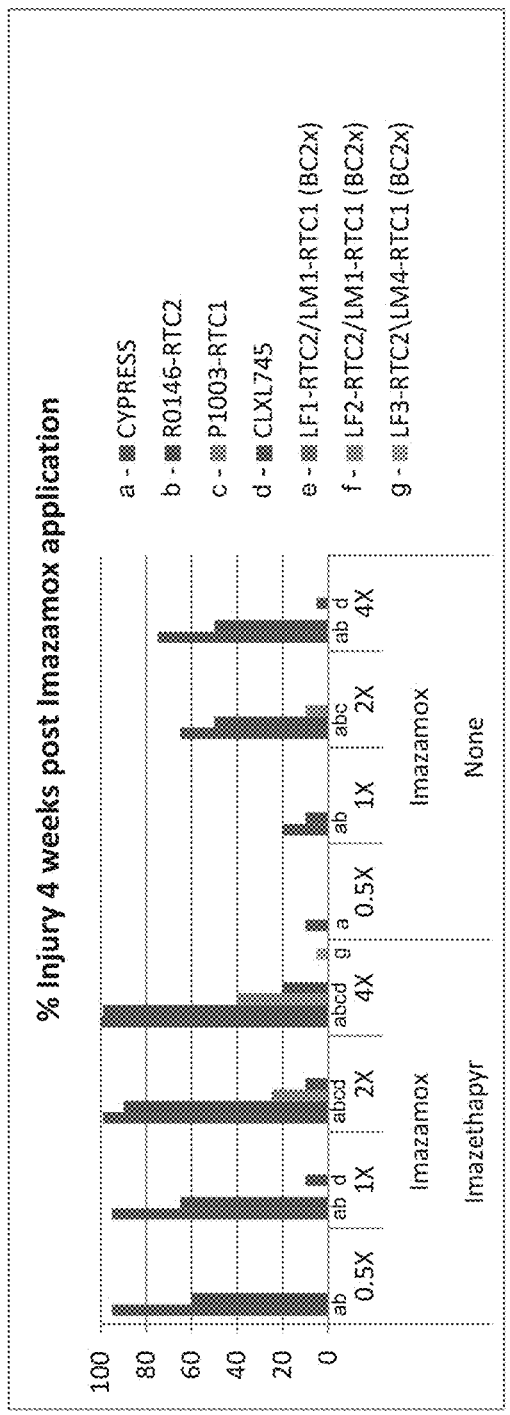

FIG. 4 Representative Pots 4 Weeks Post Application of Imazamox.

Summary:
The results of this trial indicates that RiceTec (RT) IMI hybrids show high levels of tolerance to Imazamox herbicide. No injury was observed in any of the RT IMI hybrids in any treatment. However, injury was observed in the single trait mutant lines. This was expected, because it is known that the G654E mutation only confers a weak level of tolerance to IMI herbicides. Due to the trial being conducted in the greenhouse during the difficult winter season the injury response may not have shown exactly as that of an optimal field trial, but given the consistency of response across all treatments the data indicates that RT IMI hybrids have equal or higher levels of tolerance to Imazamox than current commercial IMI hybrids.

Example 2: 16-T7: Log Sprayer Trial; Imazethapyr (See FIG. 5A, 5B, 5C, 5D; and FIG. 6)

Figure 5A:
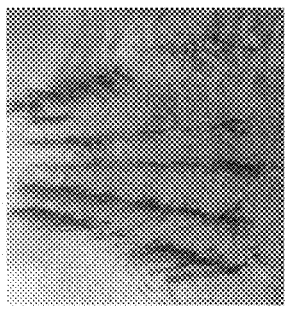
FIG. 5A to FIG. 5D illustrate the results of Example 2.
Figure 5B:
Figure 5C:
Figure 5D:
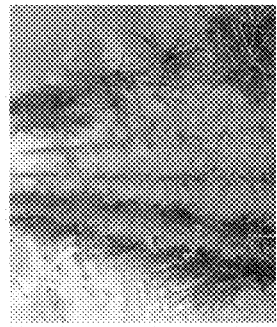
Figure 8:
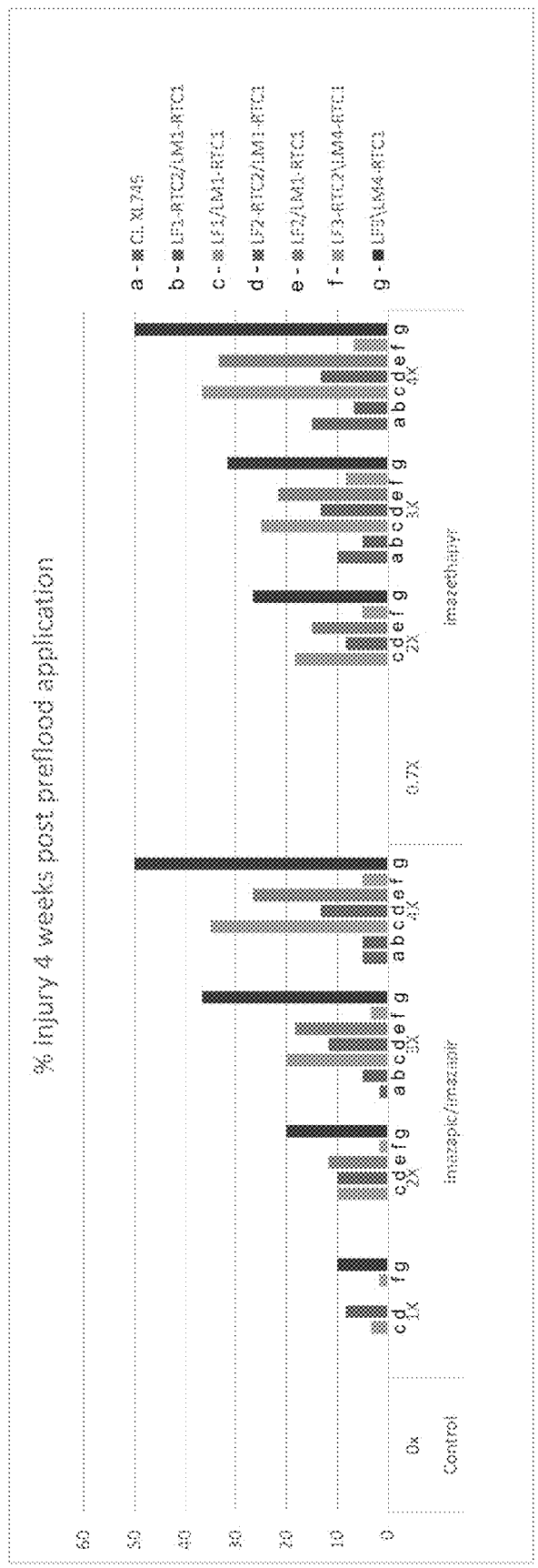

Trial:
single herbicide application at the 3-4 leaf stage using the half-step log sprayer at rates from 16× to 1/128×.
Plot Images 3 Weeks Post Application.
FIG. 5A Control, FIG. 5B 8×, FIG. 5C 1×, FIG. 5D 0.25×. Planting order L to R: P1003A205V, R0146G654E, P1003, P1003, LF2-RTC2/LM1-RTC1, LF3-RTC2\LM4-RTC1.

Figure 6:
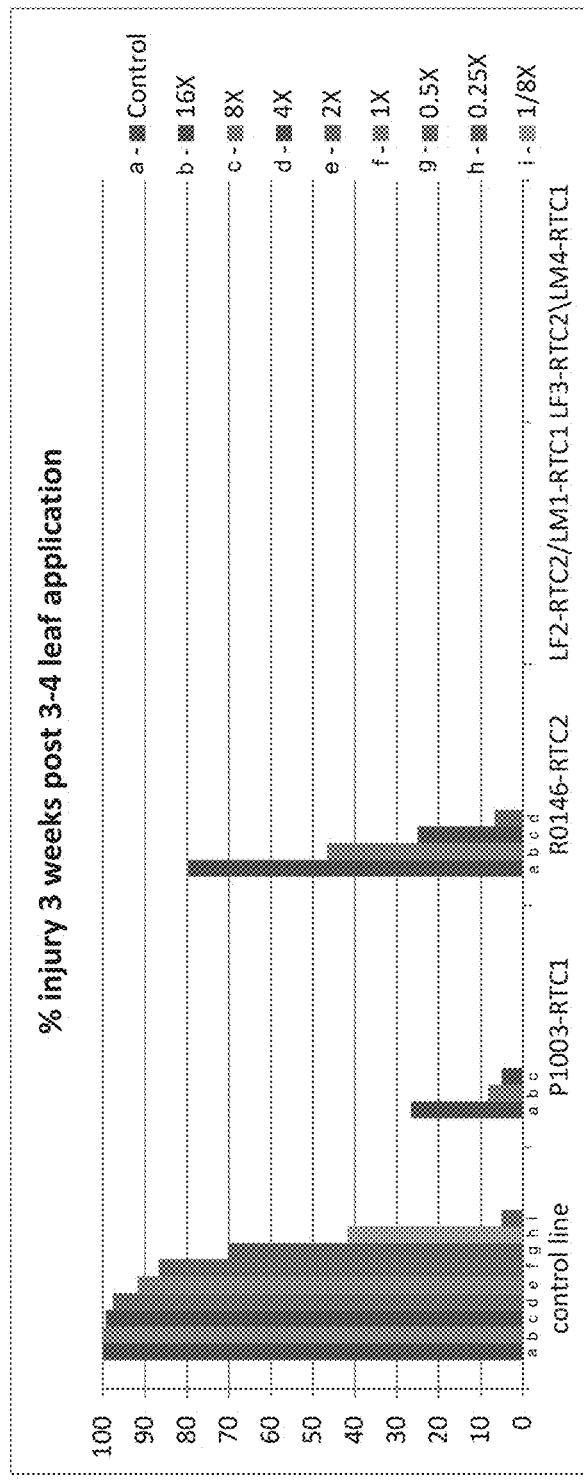
FIG. 6 graphically illustrates the results of Example 2.

Summary:
FIG. 6 shows % of injury 3 weeks post 3-4 leaf application. The homozygous A205V (RTC1) mutant line (P1003A205V) had very good tolerance to even high rates of Imazethapyr herbicide. Observed injury in the P1003A205V was below 10% at all tested rates 8× (48 oz/acre) and lower. Recorded injury in the G654E (RTC2) homozygous line was lower than expected, but this may be partially due to the later application. The G654E/A205V hybrids showed very strong levels of tolerance in this trial, with no observed injury by three weeks post application in either hybrid.

Figure 7:
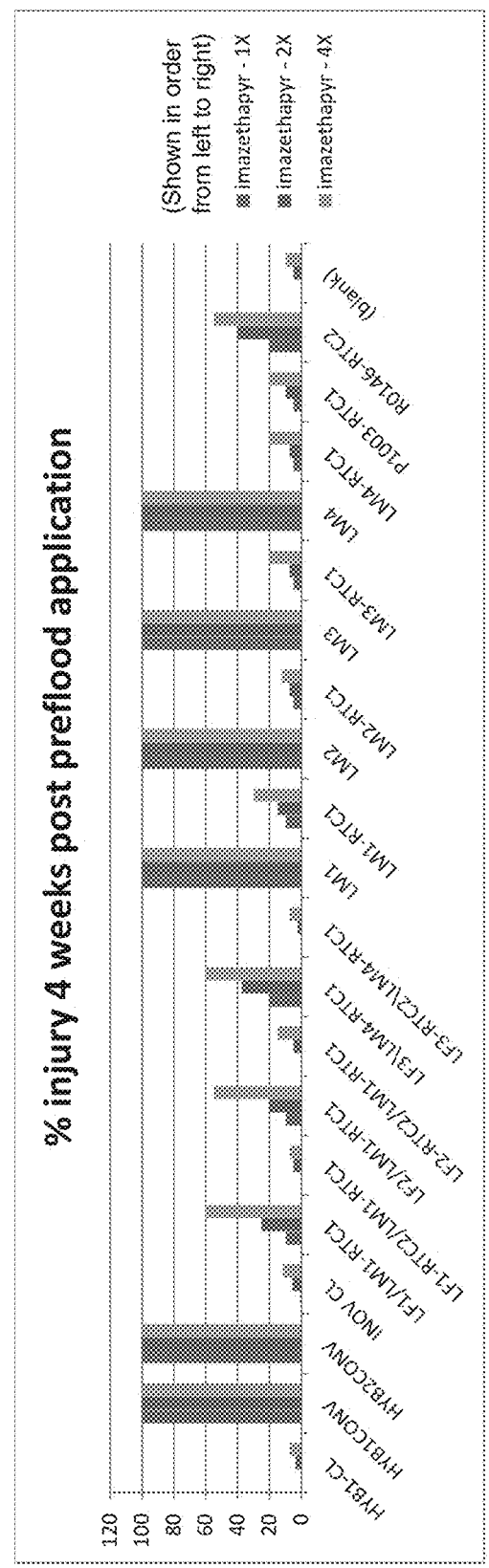
FIG. 7 graphically illustrates the results of Example 3.

Example 3: 15SA-T9: IMI Conversion Efficacy Trial of Recent IMI Conversions (See FIG. 7)

Trial:
2 leaf and preflood application of IMI herbicide on materials converted with RiceTec IMI traits and controls. All males included RTC1 (A205V) in their genome. Females with RTC2 (G654E) were not included due to limited seed numbers. Females were tested separately in 15GH-T8 using potted plant replications.

Summary:
A205V-G654E hybrids had very low injury rates in response to 2 applications of Imazethapyr. The injury observed in the RT IMI A205V-G654E hybrids was comparable to current commercial IMI hybrids. This trial supports the commercialization of the A205V-G654E hybrid. This trial was maintained through harvest.

Figure 9:
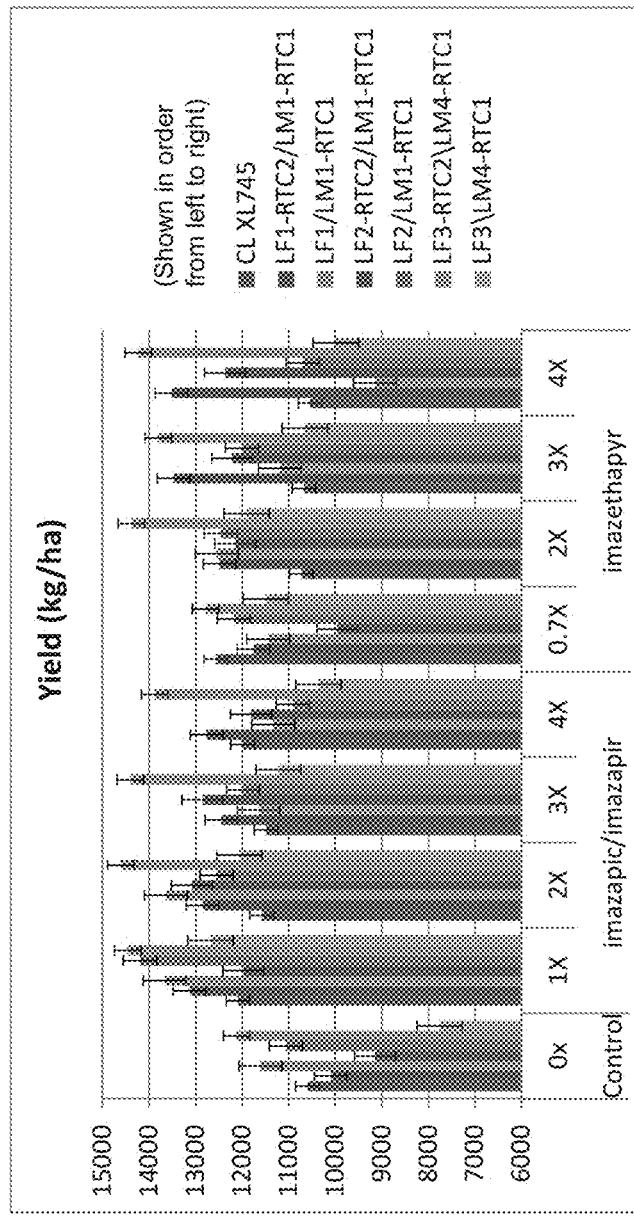
FIG. 9 is a graphical comparison of yield after various doses of IMI herbicides: control compared to various rice lines and hybrids.

Example 4: 15SA-T11: KIFIX Trial (See FIG. 8 and FIG. 9)

Trial: 2 leaf and preflood application of Imazethapyr or Kifix™ (imazapic/imazapir) herbicide on materials converted with RiceTec IMI traits and commercial IMI control.

Summary:
Injury rates observed in the converted A205V-G654E hybrids is very similar between Imazethapyr and Kifix (imazapic/imazapir) applications with slightly reduced injury observed in the equivalent Kifix treatments. Consistent with previous data, the heterozygous A205V hybrids have reduced tolerance to both herbicides as compared to the A205V-G654E hybrids. Yields of the converted hybrids was surprising in that all three of the two trait converted hybrids (A205V-G654E) performed even better than the commercial Clearfield® control (CLXL745) when herbicide was applied, with the internally developed two trait hybrids actually showing more resistance to yield loss at 4× application rates than the Clearfield® hybrid control. This supports that IMI traits prove effective in conferring tolerance to both Newpath™ for the US market as well as Kifix for Brazil with no significant yield penalty.

Figures 10A, 10B:
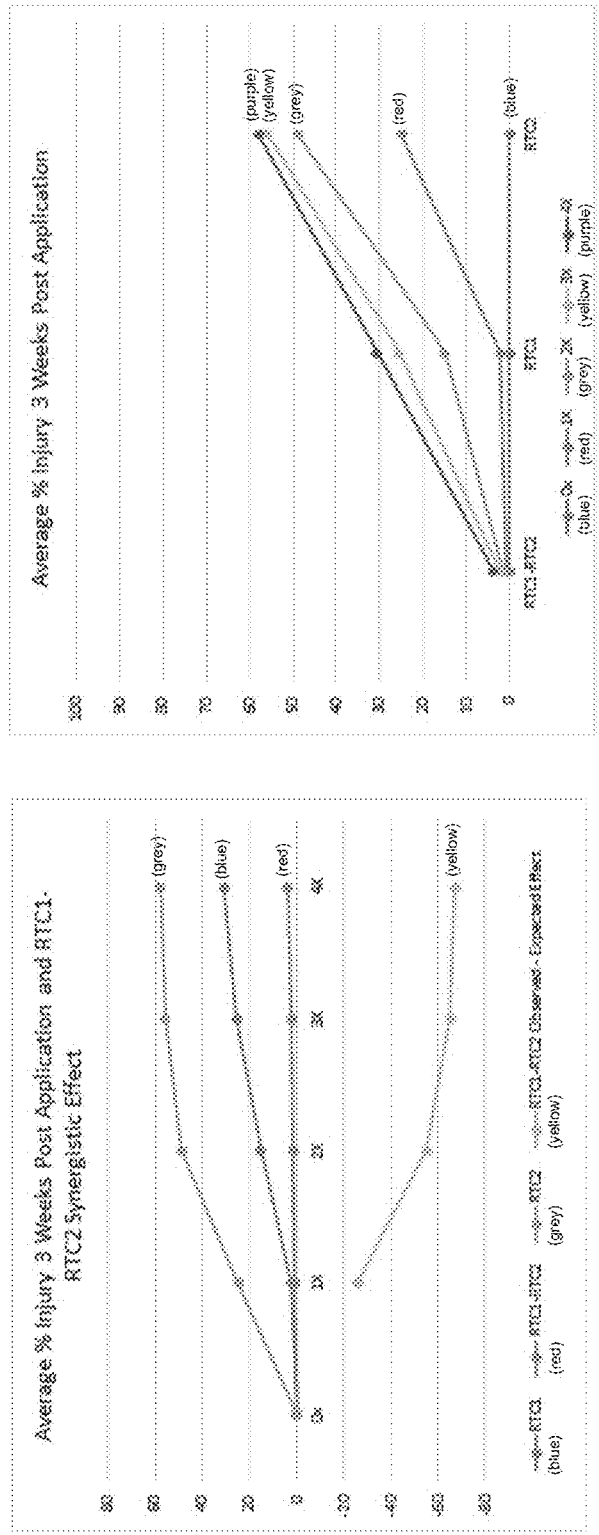
FIG. 10A and FIG. 10B show average percent injury 3 weeks post last herbicide application across trials [15SA-T11, 16-T7, 16GH-T7], which included independent experiments with single active ingredients imazetaphyr, imazamox or imazetapic, and combinations in sequential applications; Data on effects was averaged across experiments for each line, RTC1 only, RTC2 only or RTC1-RTC2; Synergistic effects of RTC1+RTC2 interactions are expressed as observed RTC1+RTC2% Injury minus expected RTC1+

Overall, FIGS. 10A and 10B show average percent injury 3 weeks post last herbicide application across trials [15SA-T11, 16-T7, 16GH-T7], which included independent experiments with single active ingredients imazetaphyr, imazamox imazetapic, in sequential applications, or unique active ingredients or in combination. Also averaged across material carrying RTC1 only, RTC2 only or RTC1-RTC2. Synergistic effects of RTC1+RTC2 interactions expressed as observed RTC1+RTC2% Injury minus expected RTC1+ RTC2% Injury calculated as [(RTC1+RTC2)−(RTC1XRTC2/100)]. (See Table 2 for Injury Rating Scale.)

Seed Deposits Under Budapest Treaty

Seed deposits of resistant/tolerant rice hybrids were deposited by RiceTec Inc. in the American Type Culture Collection (ATCC), 10801 University Boulevard, Manassas, Va. 20110, United States of America on Feb. 1, 2017. PTA accession numbers are PTA-123859, PTA-123860 and PTA-123861. (See also TABLE 1.) All restrictions will be removed upon granting of a patent, and the deposits are intended to meet all of the requirements of 37 C.F.R. §§ 1.801-1.809, and satisfy the Budapest Treaty requirements. The deposit will be maintained in the depository for a period of thirty years, or five years after the last request, or for the enforceable life of the patent, whichever is longer, and will be replaced as necessary during that period.

Definitions

In the description and tables which follow, a number of terms are used. In order to provide a clear and consistent understanding of the specification and claims, including the scope to be given such terms, the following definitions are provided:

Allele. Allele is any one of many alternative forms of a gene, all of which generally relate to one trait or characteristic. In a diploid cell or organism, the two alleles of a given gene occupy corresponding loci on a pair of homologous chromosomes.

Backcrossing. Process of crossing a hybrid progeny to one of the parents, for example, a first generation hybrid F1 with one of the parental genotypes of the F1 hybrid.

Blend. Physically mixing rice seeds of a rice hybrid with seeds of one, two, three, four or more of another rice hybrid, rice variety or rice inbred to produce a crop containing the characteristics of all of the rice seeds and plants in this blend.

Cell. Cell as used herein includes a plant cell, whether isolated, in tissue culture or incorporated in a plant or plant part.

Cultivar. Variety or strain persisting under cultivation.

Derived. As used herein means that a gene or plurality of genes is taken, obtained, received, traced, replaced or descended from a source plant or seeds, and regardless of the method used, was transferred to a different plant.

Embryo. The embryo is the small plant contained within a mature seed.

Essentially all the physiological and morphological characteristics. A plant having essentially all the physiological and morphological characteristics of the hybrid or cultivar, except for the characteristics derived from the introduced gene of interest.

Grain Yield. Weight of grain harvested from a given area. Grain yield could also be determined indirectly by multiplying the number of panicles per area, by the number of grains per panicle, and by grain weight.

Imidazolinone. "IMI" includes for example imazapyr, imazapic, imazethapyr, imazamox, imazamethabenz and imazaquin.

Injury to Plant. Is defined by comparing a test plant to controls and finding the test plant is not same height; an abnormal color, e.g. yellow not green; unusual leaf shape, curled, fewer tillers; does not survive (see Table 2).

Induced. As used herein, the term induced means genetic resistance appeared after treatment with a mutagen.

Introgress. As used herein, moving genes from a plant to another, so that the plant and its progeny carry the gene.

Locus. A locus is a position on a chromosome occupied by a DNA sequence; it confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Non-induced. As used herein, the term non-induced means genetic resistance not known to be induced; may be at different location in the genome, than an induced resistance.

Plant. As used herein, the term "plant" includes reference to an immature or mature whole plant, including a plant from which seed or grain or anthers have been removed. Seed or embryo that will produce the plant is also considered to be the plant.

Plant Part. As used herein, the term "plant part" (or a rice plant, or a part thereof) includes protoplasts, leaves, stems, roots, root tips, anthers, seed, grain, embryo, pollen, ovules, cotyledon, hypocotyl, glumes, panicles, flower, shoot, tissue, cells, meristematic cells and the like.

Progeny. Descendants of source plants obtained by breeding, recombinant or other methods, wherein genes of interest are replicated from the source plants in the descendent genes.

Pyramided. Vector stacks: when different traits are stacked in a vector, and in a single act or transformation, the traits are transmitted to the plant; the transformed plant exhibits multiple traits. Pyramiding traits: sequential transformation of single traits (all vectors are single trait carriers), or alternatively each trait is transformed in parallel, onto the same line and simple sexual crossing is used to "pyramid" them into a single line. "Either added gradually (from different donors) or added all at once (from a single multi-trait donor)."

Quantitative Trait Loci (QTL). Genetic loci that controls to some degree numerically measurable traits that are usually continuously distributed.

Recombinant/Non-Recombinant. If non-parental combination occurs, a rice patent is recombinant.

Regeneration. Regeneration refers to the development of a plant from tissue culture.

Resistance/Resistant[5]. The inherited ability of a plant to survive and reproduce following exposure to a dose of herbicide normally lethal to the wild type resistance may be naturally occurring or induced by such techniques as genetic engineering or selection of variants produced by tissue culture or mutagenesis.

[5]Weed Science Society of America, Weed Technology, vol. 12, issue 4 (October-December, 1998, p. 789)

Single Gene Converted (Conversion). Single gene converted (conversion) includes plants developed by a plant breeding technique called backcrossing wherein essentially all of the desired morphological and physiological characteristics of an inbred are recovered, while retaining a single gene transferred into the inbred via crossing and backcrossing. The term can also refer to the introduction of a single gene through genetic engineering techniques known in the art.

Source Plant or Seed. A plant or seed from which a gene or plurality of genes, is transferred to a different plant, seed, callous or other suitable recipient.

Stacking. Adding more than one thing to the same receiving entity. Methods of achieving the "stacked" state include: methods of vector-stack two or more genes in a single vector and do a single transformation to achieve stack; do sequential transformations into same receptor adding traits stepwise; achieve stacked hybrid simply by end crossing parentals carrying different traits; develop lines with multiple traits by sequential mutagenesis or crossing, and fixing the stacked state into one parent; and variants thereof.

Synergism. As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately."

The following equation may be used to calculate the expected resistance/tolerance in rice with combinations of mutations to herbicides, e.g., A and B:

$$\text{Expected} = A + B - (A \times B / 100)$$

A=observed efficacy of mutation A at the same concentration of herbicide;

B=observed efficacy of mutation B at the same concentration of herbicide.

Synergistic in the herbicide context can mean that the use of herbicide results in an increased weed control effect compared to the weed control effects of A+B that are possible with the use of each herbicide alone. Or synergistic may be considered as the resistance/tolerance level of the rice, with combined mutations (stacked) compared to effects of a rice with a single mutation.

In some embodiments, the damage or injury to the undesired vegetation caused by the herbicide is evaluated using a scale from 0% to 100%, when compared with the untreated control vegetation, wherein 0% indicates no damage to the undesired vegetation and 100% indicates complete destruction of the undesired vegetation.

Tolerance/Tolerant. The inherent ability of a species to survive and reproduce after herbicide treatment implies that there was no selection or generic manipulation to make the plant tolerant.

Resistance/tolerance are used somewhat interchangeably herein; for a specific rice plant genotype information is provided on the herbicide applied, the strength of the herbicide, and the response of the plant.

PUBLICATIONS CITED

Powles, Stephen B. and Yu, Qin, "Evolution in Action: Plants Resistant to Herbicides," Annu. Rev. Plant Biol. (2010) 61:317-347.

TABLE 1

Hybrid Rice with Both RTC1 and RTC2 in Their Genomes

| Source # | Hybrid | Designation | PTA |
|---|---|---|---|
| 15USAA04803 | S5120G654E/P1062A205V | TH1524551 | 123860 |
| 15USAA04858 | S5209G654E/P1308A205V | TH1524568 | 123859 |
| 15USAA04810 | S5107G654E/P1062A205V | TH1524558 | 123861 |

TABLE 2

Herbicide Injury Rating Scale in Rice

| Score | Rating description |
|---|---|
| 0 | no visible injury |
| 1 | injury observed in at least 1 plants but very minimal |
| 5 | minimal injury observed across plot |

TABLE 2-continued

Herbicide Injury Rating Scale in Rice

Score  Rating description

- 10   plants are stunted 10% as compared to control, or plants show herbicide injury on approximately 10% of leaf area in the plot
- 15   plants are stunted 15% as compared to control, or plants show herbicide injury on approximately 15% of leaf area in the plot
- 20   plants are stunted 20% as compared to control, or plants show herbicide injury on approximately 20% of leaf area in the plot
- 25   plants are stunted 25% as compared to control, or plants show herbicide injury on approximately 25% of leaf area in the plot
- 30   plants are stunted 30% as compared to control, or plants show herbicide injury on approximately 30% of leaf area in the plot
- 35   plants are stunted 35% as compared to control, or plants show herbicide injury on approximately 35% of leaf area in the plot
- 40   plants are stunted 40% as compared to control, or plants show herbicide injury on approximately 40% of leaf area in the plot
- 45   plants are stunted 45% as compared to control, or plants show herbicide injury on approximately 45% of leaf area in the plot
- 50   plants are stunted 50% as compared to control, or plants show herbicide injury on approximately 50% of leaf area in the plot
- 55   plants show herbicide injury on approximately 55% of leaf area in the plot
- 60   plants show herbicide injury on approximately 60% of leaf area in the plot
- 65   plants show herbicide injury on approximately 65% of leaf area in the plot
- 70   plants show herbicide injury on approximately 70% of leaf area in the plot
- 75   plants show herbicide injury on approximately 75% of leaf area in the plot
- 80   plants show herbicide injury on approximately 80% of leaf area in the plot
- 85   plants show herbicide injury on approximately 85% of leaf area in the plot
- 90   plants show herbicide injury on approximately 90% of leaf area in the plot
- 95   All plants severely injured, most are dead. Some green tissue spread throughout plot.
- 99   nearly all plants are dead, but at least 1 plant has green tissue.
- 100  all plants dead and brown. No green tissue in the plot.

TABLE 3

Yield, Grain Quality and Maturity information for deposited ATCC RTC1-RTC2 hybrids and controls

| | Hybrid/Controls | | | | | |
|---|---|---|---|---|---|---|
| | LF2-RTC2/ LM1-RTC1 | LF2/LM1-CL | LF1-RTC2/ LM1-RTC1 | LF1/LM1 | LF3-RTC2\ LM4-RTC1 | LF3\LM4 |
| ATCC# | PTA-123860 | | PTA-123861 | | PTA-123859 | |
| Yield (lbs/ac) | 10128.38 | 10234.75 | 9189.8 | 9930.19 | 10187.72 | 9967.7 |
| Lodging % | 17.4 | 20.3 | 22.8 | 19.7 | 13 | 10.0 |
| Days to 50% Heading | 82.75 | 81.63 | 81.7 | 83.6 | 86.33 | 80.3 |
| Plant Height (inches) | 114.56 | 115.44 | 122.9 | 114.46 | 123.7 | 122.9 |
| Total Mill % | 71.9 | 72.6 | 71.3 | 72 | 71.3 | 70.0 |
| Whole Mill % | 60.5 | 60.4 | 62.9 | 62.7 | 64.7 | 60.0 |
| Grain Length (mm) | 6.72 | 6.84 | 6.88 | 6.66 | 5.48 | 5.6 |
| Grain Width (mm) | 2.08 | 2.1 | 2.12 | 2.1 | 2.6 | 2.7 |
| Length Width Ratio | 3.23 | 3.26 | 3.24 | 3.17 | 2.11 | 2.1 |
| FIGS % | 6.25 | 3.2 | 2.9 | 6.25 | 2.43 | 1.9 |
| White Belly % | 13.43 | 13.35 | 10.35 | 12.62 | 5.23 | 4.5 |
| Amylose | 19.8 | 19.9 | 20.3 | 19.8 | 15.4 | 15.5 |
| ASV | 3.4 | 3.1 | 4.7 | 3.2 | 5.0 | 4.3 |
| Moisture % | 15.7 | 16.6 | 17.8 | 16.8 | 17.3 | 17.9 |
| Grain Type | Long | Long | Long | Long | Medium | Medium |

Material includes: ATTC submissions PTA-123860 [LF2-RTC2/LM1-RTC1], PTA-123861 [LF1-RTC2/LM1-RTC1], PTA-123859 [LF3-RTC2\LM4-RTC1], and their respective controls LF2/LM1-CL, LF1/LM1 and LF3\LM4. Multi-location yield performance and grain quality data is provided to demonstrate equivalency of RTC1-RTC2 products to controls carrying the same genetic base. All materials were sprayed at 2 leaf stage with 1× application of imazamox

TABLE 4

Multi-location yield and grain quality evaluation for additional RTC1-RTC2 material compared with currently commercial ClearField ® version of same hybrids. All materials were sprayed at 2 leaf stage with 1X application of imazamox.

| Material | Year | Locations | Yield cyWa | Days To Heading | Height (cm) | Grain Retention | Whole milling % | Chalk % | White Belly Chalk % | Amylose | Gel Temp. |
| --- | --- | --- | --- | --- | --- | --- | --- | --- | --- | --- | --- |
| LF2/LM1-CL | 2017 | 8 | 10235 | 83 | 115 | Good | 58 | 4 | 15 | 19 | Interm. |
| LF2-RTC2/LM1-RTC1 | 2017 | 8 | 10128 | 84 | 115 | Good | 59 | 7 | 15 | 19 | Interm. |
| LF2/LM1-CL | 2016 | 5 | 9295 | 80 | 121 | Good | 59 | 5 | 12 | 19 | Interm. |
| LF2-RTC2/LM1-RTC1 | 2016 | 5 | 8976 | 81 | 128 | Good | 57 | 7 | 15 | 19 | Interm. |
| HYB5-CL | 2017 | 5 | 9401 | 83 | 115 | Good | 59 | 7 | 17 | | Interm. |
| HYB5MG-FP | 2017 | 5 | 9189 | 81 | 123 | Excellent | 58 | 5 | 14 | | Interm. |
| HYB5-CL | 2016 | 5 | 8897 | 85 | 122 | Good | 58 | 8 | 13 | 19 | Interm. |
| HYB5MG-FP | 2016 | 5 | 8726 | 84 | 124 | Good | 56 | 8 | 15 | 20 | Interm. |
| HYB5-CL | 2016 | 7 | 8897 | 85 | 122 | Poor | 58 | 8 | 13 | 19 | Interm. |
| HYB5-FP | 2016 | 7 | 8726 | 84 | 124 | Poor | 56 | 8 | 15 | 20 | Interm. |
| HYB4-CL | 2017 | 7 | 10236 | 88 | 119 | Good | 60 | 7 | 14 | | Interm. |
| HYB4 | 2017 | 7 | 10666 | 85 | 121 | Good | 59 | 8 | 16 | | Interm. |
| HYB4-FP | 2017 | 7 | 10739 | 85 | 119 | Excellent | 59 | 8 | 15 | | Interm. |

Material includes: control commercial hybrids with ClearField® herbicide tolerance (CL suffix) and comparative pre-commercial hybrids with same parental source but carrying the RTC1–RTC2 (FP suffix) herbicide tolerance mutations. Clearfield® hybrids carry the IMI mutation localized in position 653.

We claim:

1. A rice plant grown from a seed deposited under ATCC accession number PTA-123859, PTA-123860, or PTA-123861.

2. A progeny plant of the plant grown from the seed of claim 1, wherein the progeny plant is F1 generation progeny.

* * * * *